United States Patent [19]
Hibst et al.

[11] Patent Number: 6,084,126
[45] Date of Patent: Jul. 4, 2000

[54] OXIDATION USING MULTIMETAL MOLYBDENUM AND VANADIUM OXIDES

[75] Inventors: Hartmut Hibst, Schriesheim; Andreas Tenten, Maikammer; Laszlo Marosi, Ludwigshafen, all of Germany

[73] Assignee: BASF Aktiengesellshaft, Ludwigshafen, Germany

[21] Appl. No.: 09/092,181

[22] Filed: Jun. 5, 1998

Related U.S. Application Data

[62] Division of application No. 08/744,246, Nov. 5, 1996, Pat. No. 5,807,531.

[30] Foreign Application Priority Data

Nov. 16, 1995 [DE] Germany ............... 19542755

[51] Int. Cl.⁷ .................................. C07C 51/16
[52] U.S. Cl. .................. 562/535; 407/523; 407/538; 407/542
[58] Field of Search .................. 562/535, 407, 562/523, 538, 542

[56] References Cited

U.S. PATENT DOCUMENTS

| | | |
|---|---|---|
| 4,014,925 | 3/1977 | Ferlazzo et al. |
| 4,208,306 | 6/1980 | Childress et al. |
| 5,270,277 | 12/1993 | Hums |

FOREIGN PATENT DOCUMENTS

| | | |
|---|---|---|
| 0 293 859 | 12/1988 | European Pat. Off. |
| 0 575 897 | 12/1993 | European Pat. Off. |
| 0 609 750 | 8/1994 | European Pat. Off. |
| 0 668 102 | 8/1995 | European Pat. Off. |
| WO 96/27437 | 9/1996 | WIPO |

*Primary Examiner*—Paul J. Killos
*Assistant Examiner*—Robert W. Deemie
*Attorney, Agent, or Firm*—Oblon, Spivak, McClelland, Maier & Neustadt, P.C.

[57] ABSTRACT

A method for gas-phase oxidation of an organic compound such as acrolein is provided, which includes oxidizing the organic compound with an oxidizing agent in the presence of a catalyst, to produce a product such as acrylic acid, wherein the catalyst includes a multimetal oxide material having at least two phases and of the formula III $$\{A\}_p\{B\}_q \quad (III),$$

wherein $$A = (Mo_{12-a-b-c}V_aM^1_bM^2_cO_x) \times \frac{12}{12-a-b-c} \quad \text{(active phase)},$$

$$B = M^3_{12}Cu_dH_eO_y \quad \text{(promoter phase)},$$

$M^1$, $M^2$, $a$, $b$, $c$, $x$, $M^3$, $d$, $e$, $y$, $p$ and $q$ are defined in the claims, which contains the moiety $\{A\}_p$ in the form of three-dimensional regions A which are delimited from their local environment owing to their chemical composition differing from their local environment and are of the chemical composition $$A \ Mo_{12-a-b-c}V_aM^1_bM^2_cO_x$$

and the moiety $\{B\}_q$ in the form of three dimensional regions B which are delimited from their local environment owing to their chemical composition differing from their local environment and are of the chemical composition $$B \ M^3_{12}Cu_dH_eO_y$$

where the regions A and B are distributed relative to one another as in a mixture of finely divided A and finely divided B and, with the use of CuKα radiation ($\lambda$=1.54178 Å), the three-dimensional atomic arrangement of the regions A gives an X-ray powder diffraction spectrum (the intensity of the diffracted X-rays plotted as a function of twice the diffraction angle (2Θ)) which, in the 2Θ range from 5 to 50°, contains the diffraction lines $A^1$, $A^3$, $A^5$, $A^9$ and $A^{10}$ but not more than diffraction lines $A^1$ to $A^{10}$ defined in the claims.

10 Claims, 19 Drawing Sheets

OXIDATION USING MULTIMETAL MOLYBDENUM AND VANADIUM OXIDES

This application is a Division of application Ser. No. 08/744,246 filed on Nov. 5, 1996 U.S. Pat. No. 5,807,531.

The present invention relates to multimetal oxides of the general formula I $$Mo_{12-a-b-c} V_a M^1_b M^2_c O_x \qquad (I),$$

where $M^1$ is W and/or Nb, $M^2$ is from 0.1 to 6, preferably from 0.5 to 4.5, b is from 0 to 6, preferably from 0.1 to 6, particularly preferably from 0.5 to 4, c is from 0 to 6, frequently from 0.1 to 6 or from 0.5 to 4, with the proviso that a+b+c is from 0.1 to 6, preferably from 0.5 to 4.5, and x is a number which is determined by the valency and frequency of the elements in I other than oxygen, whose three-dimensional atomic arrangement obtained using CuKα radiation (λ=1.54178 Å) gives an X-ray powder diffraction spectrum (the intensity A of the diffracted X-rays plotted as a function of twice the diffraction angle ($2\Theta$)) which contains, in the $2\Theta$ range (stated in the unit for angles in a plane: °=degree) from 5 to 50°, at least the following characteristic diffraction lines $A^1, A^3, A^5, A^9$ and $A^{10}$, but at most the following diffraction lines $A^1$ to $A^{10}$:

| X-ray diffraction line | 2Θ [°] |
|---|---|
| $A^1$ | 8.3 ± 0.7 |
| $A^2$ | 14.4 ± 0.7 |
| $A^3$ | 22.3 ± 0.2 |
| $A^4$ | 23.5 ± 0.7 |
| $A^5$ | 27.2 ± 0.4 |
| $A^6$ | 32.0 ± 0.8 |
| $A^7$ | 34.8 ± 0.6 |
| $A^8$ | 38.7 ± 0.5 |
| $A^9$ | 45.4 ± 0.4 |
| $A^{10}$ | 48.8 ± 0.4 |

The wavelength λ of the X-radiation used for the diffraction and the diffraction angle $\Theta$ are related to one another by the Bragg relationship:

$$2 \sin \Theta = \lambda/d,$$

where d is the interplanar spacing of the three-dimensional atomic arrangement, associated with the respective diffraction line.

Furthermore, the present invention relates to a process for the preparation of multimetal oxides I and their direct use as active material of catalysts for the catalytic gas-phase oxidation of organic compounds.

The present invention also relates to the use of multimetal oxides I as starting compounds for the preparation of multimetal oxide materials which contain Mo and V and in turn are suitable as active material for the catalytic gas-phase oxidation of organic compounds.

The preparation of multimetal oxide materials containing Mo and V and their use as active materials of catalysts for the catalytic gas-phase oxidation of organic compounds (eg. acrolein to acrylic acid) is generally known (eg. EP-A 293 859).

Initially, the preparation of such multimetal oxide materials containing Mo and V was carried out by providing a suitable source (starting compound) of each of their elemental constituents, producing from the total amount of these sources a very thorough, preferably finely divided dry mixture having a composition corresponding to the required stoichiometry of the desired multimetal oxide material and calcining said dry mixture at elevated temperatures for several hours under inert gas or under an oxygen-containing gas (eg. air) (single-vessel process). All that was important with regard to the sources of the elemental constituents of the multimetal oxide materials was that they were either already oxides or compounds convertible into oxides by heating, at least in the presence of oxygen (cf. for example DE-A 4 335 973 and U.S. Pat. No. 4,035,262).

It is now known (cf. for example EP-A 835, DE-C 3 338 380, DE-A 4 220 859, DE-A 4 307 381, DE-A 4 405 085, DE-A 4 405 059, DE-A 4 405 060, DE-A 4 405 514 and DE-A 44 404 891) that it may be advantageous first to preform separately a multimetal oxide comprising only a fraction of the total amount of the elemental constituents of the desired multimetal oxide material and then to use this separately preformed fractional multimetal oxide as a finely divided source for producing the desired multimetal oxide material.

As a rule, this results in multimetal oxide materials which have a multiphase composition and some of which are more advantageous for the catalytic gas-phase oxidation of organic compounds than the multimetal oxide materials prepared by the single-vessel processes known per se. It is an object of the present invention to provide novel fractional metal oxides of multimetal oxide materials containing Mo and V, which multimetal oxide material can be used as starting compounds for the preparation of multiphase multimetal oxide materials which contain Mo and V and are particularly suitable as active material for the gas-phase catalytic oxidation of acrolein to acrylic acid.

We have found that this object is achieved by the multimetal oxides I defined at the outset. Advantageous multimetal oxides I include those in which x is from 15 to 50. x is preferably from 25 to 40, particularly preferably from 30 to 40. Other suitable multimetal oxides I include those in which c is 0. Where c is 0 and $M^1$ is exclusively W, suitable multimetal oxides I are those in which ≧25 or ≧50 or ≧75 or ≧95 or ≧99% of the vanadium is present as $V^{4+}$.

Typical of the novel multimetal oxides I is that their X-ray powder diffraction spectrum obtained using CuKα radiation in the $2\Theta$ range from 5° to 50° as a characteristic fingerprint contains at least the diffraction lines $A^1, A^3, A^5, A^9$ and $A^{10}$ but on no account more than the diffraction lines $A^1, A^2, A^3, A^4, A^5, A^6, A^7, A^8, A^9$ and $A^{10}$. It is noteworthy that some of the diffraction lines are those which have a relatively large half-width FWHM (the width of the diffraction line (the intensity plotted as a function of 2θ) at half the height of their maximum amplitude, stated in the unit for angles in a plane), reflecting an unusual pattern of short-range and long-range order in the novel multimetal oxides I (cf. Examples). In the author's opinion, this particular pattern of short-range and long-range order is responsible, inter alia, for the particular catalytic properties of the novel multimetal oxides I.

Owing to the particular half-width conditions, the X-ray powder diffraction spectrum of the novel multimetal oxides I does not contain the diffraction lines $A^i$ in completely resolved form. However, the presence of the multiplicity of diffraction lines $A^i$ (after subtraction of the linear background) is directly visually evident as a relative maximum in the envelope of the X-ray powder diffraction spectrum of the novel multimetal oxides I, the position of these relative maxima defining, in this publication, the position of the diffraction lines $A^i$ according to the claims.

After subtraction of the linear background (the connecting line between $A(2\Theta=5°)$ and $A(2\Theta=65°)$), the following relative line intensities ($I_A^{rel}=(I/I_o)\times 100\%$), based on the most intense of the diffraction lines $A^1$ to $A^{10}$, can be furthermore assigned to these diffraction lines $A^1$ to $A^{10}$, the amplitude, measured from the base line to the relative maximum, being used as a measure of the intensity:

| X-ray diffraction line | $I_A^{rel}$ (%) |
|---|---|
| $A^1$ | 7 ± 5 |
| $A^2$ | 5 ± 5 |
| $A^3$ | 100 |
| $A^4$ | 40 ± 40 |
| $A^5$ | 70 ± 40 |
| $A^6$ | 25 ± 25 |
| $A^7$ | 20 ± 20 |
| $A^8$ | 10 ± 10 |
| $A^9$ | 25 ± 15 |
| $A^{10}$ | 35 ± 20 |

With regard to this line intensity data, it should be noted that, in contrast to the position of the lines, the relative line intensities are markedly influenced in a manner known per se to a person skilled in the art by the individual crystal orientations obtained in various powder preparation and based on the anisotropy of the crystal form and are therefore of little significance for identification of the novel multimetal oxides.

In this connection, it should be stated that observation has shown that a further characteristic of the CuKα X-ray powder diffraction spectrum of the novel multimetal oxides I appears to be the fact that it generally contains no diffraction lines whose FWHM<0.25°.

In all embodiments, the X-ray powder diffraction spectrum was recorded by means of a Siemens D-5000 diffractometer using CuKα radiation (40 kV, 30 mA, λ=1.54178 Å). The diffractometer was equipped with an automatic primary and secondary collimator and with a graphite secondary monochromator.

It is of course possible to resolve the X-ray powder diffraction spectrum of the multimetal oxides I, and hence to produce an alternative characterization of said spectrum, by subtracting the linear background and then, under the boundary condition of a minimum mean square deviation, describing the experimental diffraction spectrum (its envelope) by a mathematical function and converting it by resolution into a superposition of separately resolved lines $A^{1*}$ to $A^{10*}$. The maximum of each of the resolved lines defines their line position.

The resolution of the X-ray powder diffraction spectra, as described above, was carried out using the 1994 version of the software package DIFFRAC-AT V 3.2/PROFILE supplied by Siemens, the resolution and fitting being carried out on the basis of the Pearson VII form function.

While the presence of the diffraction lines $A^2$, $A^4$ and $A^6$ to $A^8$ in the CuKα X-ray powder diffraction spectra of the novel multimetal oxides I on the basis of an exclusively visual consideration of their envelope entails a certain degree of uncertainty in some cases and may therefore be contentious (cf. Example), their mathematical resolution produced as described above generally unambiguously indicates diffraction lines $A^{2*}$, $A^{4*}$, $A^{6*}$ and $A^{7*}$ (cf. Example), whereas it does not require a diffraction line $A^{8*}$. Both methods of characterization (piece of information) together therefore require the definition, according to the claims, of the subject of the invention. On the other hand, when exclusively mathematically resolved, the CuKα X-ray powder diffraction spectrum of the novel multimetal oxides I can as a rule be characterized as follows:

| X-ray diffraction iine | 2Θ [°] | $I_F^{rel}$ [%] | FWHM [°] |
|---|---|---|---|
| $A^{1*}$ | 8.1 ± 0.7 | 8 ± 7 | 3.0 ± 0.8 |
| $A^{2*}$ | 14.0 ± 0.8 | 6 ± 5 | 2.4 ± 1.5 |
| $A^{3*}$ | 22.2 ± 0.2 | 30 ± 20 | 1.2 ± 0.9 |
| $A^{4*}$ | 23.2 ± 0.7 | 23 ± 20 | 1.8 ± 1.2 |
| $A^{5*}$ | 27.0 ± 0.5 | 80 ± 20 | 4.0 ± 2.5 |
| $A^{6*}$ | 31.8 ± 1.5 | 52 ± 48 | 5.0 ± 3.0 |
| $A^{7*}$ | 34.7 ± 1.2 | 52 ± 48 | 4.0 ± 3.0 |
| $A^{8*}$ | — | — | — |
| $A^{9*}$ | 45.4 ± 0.4 | 12 ± 8 | 1.5 ± 1.0 |
| $A^{10*}$ | 48.6 ± 0.5 | 25 ± 20 | 2.2 ± 1.8 |

$I_F^{rel}$ [%] is the percentage line intensity based on the most intense of the diffraction lines $A^{1*}$ to $A^{10*}$, the area under the diffraction line being used as the measure of intensity.

Figure 1:
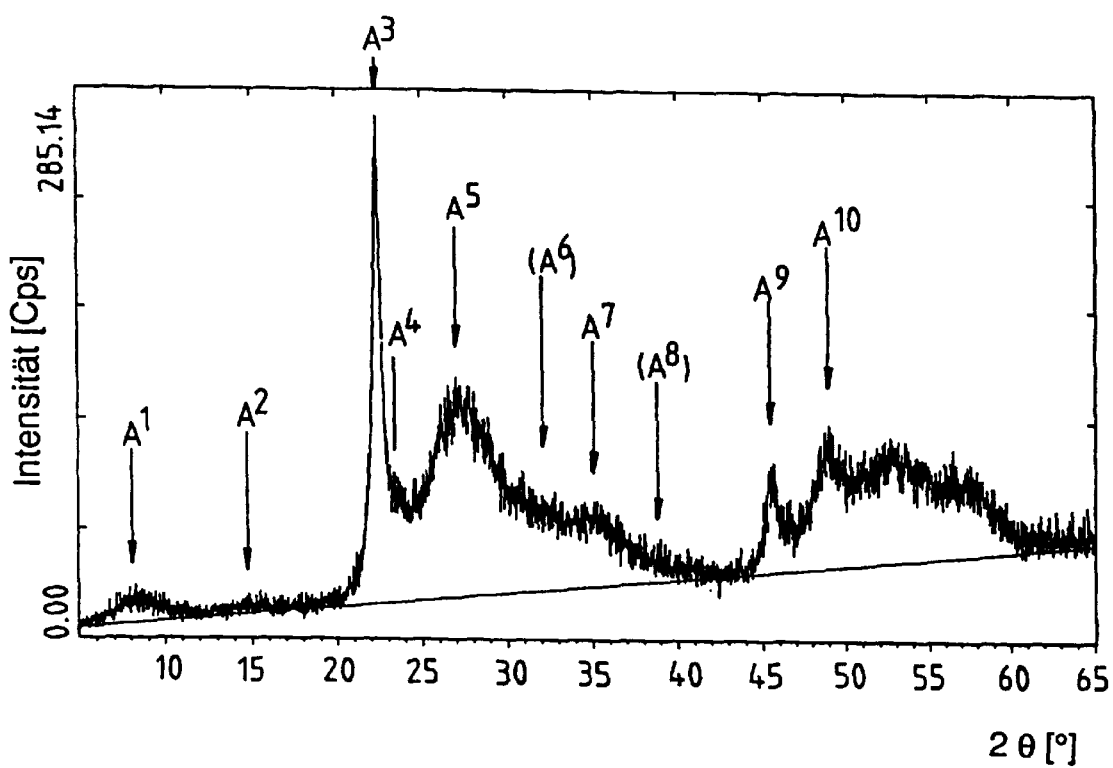
FIG. 1 shows the Cu Kα X-ray powder diffraction pattern of a multimetal oxide of the present invention.

The novel multimetal oxides I are obtainable in a simple manner by producing, from suitable source of their elemental constituents, a very thorough, preferably finely divided, dry mixture which corresponds to the desired stoichiometry, and calcining this mixture at from 300 to 500° C. The key to obtaining the novel multimetal oxides I is the redox character of the calcination atmosphere, which must not be too oxidizing and must not be too reducing.

It is not possible to provide generally valid quantitative data with regard to the required redox character of the calcination atmosphere. Thus, on the one hand the required redox character varies with the chosen stoichiometry and on the other hand, for example, the opposite ions (eg. $NH_4\oplus$) of the chosen sources of the elemental constituents also contribute to the redox character of the calcination atmosphere, for example when they are decomposed during the calcination. By exploratory preliminary experiments, a person skilled in the art can, however, determine the required redox character of the calcination atmosphere.

For controlling the redox character of the calcination atmosphere, a person skilled in the art has available, for example, $N_2$ and/or noble gases, as inert gases, for example ammonia, hydrogen, lower molecular weight aldehyde and/or hydrocarbons as reducing gases and oxygen (generally in the form of air) as an oxidizing gas. All that is important with regard to the elemental sources is that they are either already oxides or are compounds which can be converted into oxides by heating, at least in the presence of oxygen. In addition to the oxides, particularly suitable starting compounds are therefore halides, nitrates, formates, citrates, oxalates, acetates, carbonates and hydroxides. Suitable starting compounds of Mo, V, W and Nb are also their oxo compounds (molybdates, vanadates, tungstates and niobates), which as a rule have $NH_4^{\oplus}$ as the opposite ion, which, on heating, liberates $NH_3$ having a reducing action. The acids derived from these oxo compounds are of course also suitable as possible starting compounds. In addition, compounds such as ammonium acetate and ammonium nitrate are frequently added to the elemental sources and act as pore formers during the calcination and also influence the redox character of the calcination atmosphere.

The thorough mixing of the starting compounds in the preparation of multimetal oxides I can be carried out in dry or wet form. If it is effected in dry form, the starting compounds are advantageously used as finely divided powders and are subjected to calcination after mixing and, if required, compaction. However, the thorough mixing is preferably carried out in the wet form. Usually, the starting compounds are mixed with one another in the form of an aqueous solution and/or suspension. The aqueous material is then dried and is calcined after drying. The drying process is preferably carried out immediately after the preparation of the aqueous mixture and by spray drying (the entry temperature is as a rule from 250 to 350° C. and the outlet temperatures are usually from 100 to 150° C.).

Interestingly, the novel multimetal oxides I as such are suitable as active material of catalysts for the gas-phase catalytic oxidation of organic compounds, such as alkanes, alkanols, alkenes, alkanals, alkenals and alkenols of 3 to 6 carbon atoms (eg. propylene, methacrolein, tert-butanol, methyl ester of tert-butanol, isobutene, isobutane or isobutyraldehyde), to olefinically unsaturated aldehydes and/or carboxylic acids, and to the corresponding nitriles (ammoxidation, especially or propene to acrylonitrile and of isobutene or tert-butanol to methacrylonitrile). The preparation of acrolein, methacrolein and methacrylic acid may be mentioned by way of example. They are also suitable as catalyst active materials for the oxidative dehydrogenation of olefinic compounds. Without a doubt, the multimetal oxides I are particularly suitable as active material of catalysts for the gas-phase catalytic oxidation of acrolein to acrylic acid, its high activity being particularly striking with regard to this reaction.

When the novel multimetal oxide materials are used as active material of catalysts for the gas-phase catalytic oxidation of organic compounds, in particular acrolein to acrylic acid, shaping to achieve the desired catalyst geometry is preferably carried out by application to premolded inert catalyst carriers, before or after the final calcination. The usual carriers, such as porous or nonporous alumines, silica, thorium dioxide, zirconium dioxide, silicon carbide or silicates, such as magnesium silicate or aluminum silicate, may be used. The carrier elements may be regularly or irregularly shaped, regularly shaped carrier elements having pronounced surface roughness, for example spheres or hollow cylinders, being preferred. Among these in turn, spheres are particularly advantageous. The use of essentially nonporous, spherical carriers having surface roughness and comprising steatite, whose diameter is from 1 to 6 mm, preferably from 4 to 5 mm, is particularly advantageous. The layer thickness of the active material is advantageously chosen in the range from 50 to 500 $\mu$m, preferably from 150 to 250 $\mu$m. It should be pointed out here that, in the preparation of such coated catalysts, the powder material to be applied is generally moistened for coating of the carrier elements and is dried again after application, for example by means of hot air.

For the preparation of the coated catalysts, the coating of the carrier elements is as a rule carried out in a suitable rotatable container, as disclosed, for example, in DE-A 2 909 671 or EP-A 293 859. As a rule, the relevant material is calcined before the carrier is coated. Furthermore, the catalytically active material is milled to a particle diameter of from >0 to 300 $\mu$m, preferably from 0.1 to 200 $\mu$m, particularly preferably from 0.5 to 50 $\mu$m, before the coating process is carried out. The coating and calcination process can also be carried out in a suitable manner according to EP-A 293 859, so that the resulting multimetal oxide I layers have a specific surface area of from 0.50 to 150 $m^2/g$, a specific pore volume of from 0.10 to 0.90 $cm^3/g$ and a pore diameter distribution such that at least 10% of the total pore volume are accounted for by each of the diameter ranges from 0.1 to <1 $\mu$m, from 1.0 to <10 $\mu$m and from 10 $\mu$m to 100 $\mu$m. The pore diameter distributions stated as being preferred in EP-A 293 859 may also be established. The novel multimetal oxides I can of course also be used as unsupported catalysts. In this context, the thorough dry mixture comprising the starting compounds of the multimetal oxide I is preferably compacted immediately to give the desired catalyst geometry (for example, pelletizing or extrusion), it being possible, if required, to add conventional assistants, eg. graphite or stearic acid, as lubricants and/or molding aids and reinforcing agents, such as microfibers of glass, asbestos, silicon carbide or potassium titanate, and calcination is effected. Here too, calcination can generally be carried out prior to the shaping procedure.

A preferred geometry of unsupported catalysts comprises hollow cylinders having an external diameter and a length of from 2 to 10 mm and a wall thickness of from 1 to 3 mm.

For the catalytic gas-phase oxidation of acrolein to acrylic acid using the novel multimetal oxides I as catalyst active material, acrolein produced by the catalytic gas-phase oxidation of propene is usually used. As a rule, the acrolein-containing reaction gases from this propene oxidation are used without intermediate purification. The gas-phase catalytic oxidation of acrolein is usually carried out in tube-bundle reactors, as a heterogeneous fixed-bed oxidation. Oxygen, advantageously diluted with inert gases (for example in the form of air), is used as the oxidizing agent in a manner known per se. Suitable diluents are, for example, $N_2$, $CO_2$, hydrocarbons, such as methane, ethane, propane, butane and/or pentane, recycled reaction exit gases and/or steam. As a rule, an acrolein:oxygen:steam:inert gas volume ratio of 1: (1 to 3): (0 to 20): (3 to 30), preferably 1: (1 to 3): (0,5 to 10): (7 to 18), is established in the acrolein oxidation. The reaction pressure is in general from 1 to 3 bar and the total space velocity is preferably from 100 to 3500 l (S.T.P.) per 1 per h. Typical multitube fixed-bed reactors are described, for example, in DE-A 2 830 765, DE-A 2 201 528 or U.S. Pat. No. 3,147,084. The reaction temperature is usually chosen so that the acrolein conversion in a single pass is above 90%, preferably above 98%. Usually, reaction temperatures of from 230 to 330° C. are required in this connection.

It is noteworthy that, in the gas-phase catalytic oxidation of acrolein to acrylic acid, the novel multimetal oxides I have not only a high activity but also a surprisingly short forming time, ie. if a tube-bundle reactor loaded with the novel multimetal oxides I is operated under the abovementioned conditions using an acrolein-containing gas stream for the purpose of the oxidative formation of acrylic acid, the selectivity of the acrylic acid formation reaches its plateau value within a shorter operating time. With regard to this plateau value, the preparation of the novel multimetal oxide materials exhibits higher reproducibility.

However, the multimetal oxides I begin fully to display their potential as catalyst active material for the catalytic gas-phase oxidation of organic compounds, in particular of acrolein to acrylic acid, while retaining the abovementioned advantages, only when they are diluted with multimetal oxides of the general formula II

where
$M^3$ is Mo, W, V, Nb and/or Ta,
d is from 4 to 30, preferably from 6 to 24, particularly preferably from 9 to 17,
e is from 0 to 20, preferably from 0 to 10, and
y is a number which is determined by the valency and frequency of the elements other than oxygen in II, to give at least two-phase multimetal oxide materials of the general formula III

where

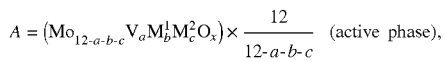

and
p and q are numbers other than zero, whose ratio p/q is from 160:1 to 1:1, preferably from 20:1 to 1:1, particularly preferably from 15:1 to 4:1, which contain the moiety $[A]_p$ in the form of three-dimensional regions A which are delimited from their local environment owing to their chemical composition differing from their local environment and are of the chemical composition $$A\ Mo_{12-a-b-c}\ V_a\ M_b^1\ M_c^2\ O_x$$

and the moiety [B] in the form of three-dimensional regions B which are delimited from their local environment owing to their chemical composition differing from their local environment and are of the chemical composition $$B\ M_{12}^3\ Cu_d\ H_e\ O_y$$

the regions A and B being distributed relative to one another as in a mixture of finely divided A and finely divided B.

In the simplest procedure for the preparation of such multimetal oxide materials III, the multimetal oxides I and II are each preformed separately, and a thorough dry mixture is then produced from at least one finely divided, separately preformed multimetal oxide I and at least one finely divided, separately preformed multimetal oxide II in the desired ratio (the thorough mixing can be carried out in dry or wet form; if it is effected in wet, as a rule aqueous, form, drying is carried out subsequently; the mixing can be carried out by means of a kneader or mixer), from which dry mixture suitable catalysts for the catalytic gas-phase oxidation of organic compounds, in particular that of acrolein to acrylic acid, can then be produced in a manner corresponding to that described for the multimetal oxide I alone, by shaping. However, both the multimetal oxides I and the multimetal oxide materials III can of course also be used in powder form as catalysts. It is just as self evident that the multimetal oxide materials III can be used for all those catalytic gas-phase reactions for which the multimetal oxides I were also stated as being suitable. If catalysts based on multimetal oxide materials III as active material are used for the catalytic gas-phase oxidation of acrolein to acrylic acid, this is generally effected under the same process conditions as described for the corresponding use of the multimetal oxide I catalysts alone. The multimetal oxides II can be prepared in a simple manner known per se to a person skilled in the art, for example by producing a very thorough, preferably finely divided, dry mixture from suitable sources of their elemental constituents and calcining this dry mixture at from 200 to 1000° C., frequently from 250 to 600° C., often from 300 to 500° C., it being possible to carry out the calcination under inert gas (eg. $N_2$, a mixture of inert gas and oxygen (eg. air), reducing gases, such as hydrocarbons (eg. methane), aldehydes (eg. acrolein) or ammonia, but also under a mixture of $O_2$ and reducing gases (eg. all of the abovementioned ones), as described, for example, in DE-A 4 335 973. It is note-worthy that the calcination atmosphere here may also comprise steam. In the case of a calcination under reducing conditions, it should be noted that the metallic constituents are not reduced to the element. The calcination time generally decreases with increasing calcination temperature.

Essentially the same statements as those made for the sources of the elemental constituents of the multimetal oxides I are applicable with regard to the sources of the elemental constituents of the multimetal oxides II. Here too, all that is essential is that they are either oxides or compounds which can be converted into oxides by heating, at least in the presence of oxygen. In a preferred preparation method for the multimetal oxides II, the thermal treatment of the thorough mixture of the starting compounds used is carried out in an autoclave in the presence of steam under superatmospheric pressure at from >100 to 600° C.

Depending on the chosen calcination conditions, the resulting multimetal oxides II have different three-dimensional atomic arrangements. All those multimetal oxides II which are described in DE-A 4 405 514, DE-A 4 440 891 and DE-A 19 528 646 as a possible key phase or promoter phase are particularly suitable for the present invention, ie. advantageous multimetal oxides II include those which have the structure type, (the X-ray diffraction pattern) of at least one of the copper molybdates listed in Table 1 below (the expression in brackets indicates the source of the associated X-ray diffraction fingerprint):

| | |
|---|---|
| 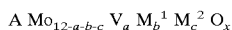 | (Lindgrenite, index card 36–405 of the JCPDS-ICDD index (1991)), |
| 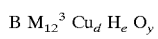 | (A. Moini et al., Inorg. Chem. 25(21) (1986) page 3782 to 3785), |

| | |
|---|---|
| $Cu_4Mo_5O_{17}$ | (Index card 39–181 of the JCPDS-ICDD index (1991)), |
| $Cu_6Mo_5O_{18}$ | (Index card 40–865 of the JCPDS-ICDD index (1991)), |
| $Cu_6Mo_4O_{15}$ | (Index card 35–17 of the JCPDS-ICDD index (1991)), |
| $CuMoO_4$ | (Index card 22–242 of the JCPDS-ICDD index (1991)), |
| $CuMoO_4$ | (Russian Journal of Inorganic Chemistry 36(7) (1991), 927–928, Table 1, $CuMoO_4$-III with distorted wolframite structure ($CuWO_4$, index card 21–307 of the JCPDS-ICDD index (1994)), |
| $CuMoO_4$ | (Index card 26–546 of the JCPDS-ICDD index (1991)), |
| HT-Cu molybdate | (DE-A 19 528 646), |
| $Cu_{4-x}Mo_3O_{12}$ | where x is from 0 to 0.25 (index cards 24–56 and 26–547 of the JCPDS-ICDD index (1991)), |
| $Cu_3Mo_2O_9$ | (Index cards 24–55 and 34–637 of the JCPDS-ICDD index (1991)) and |
| $Cu_2MoO_5$ | (Index cards 22–607 of the JCPDS-ICDD index (1991)). |

Multimetal oxides II to be recommended for the preparation of multimetal oxide materials III which are particularly suitable for the catalytic gas-phase oxidation of acrolein to acrylic acid are those of the general formula IV

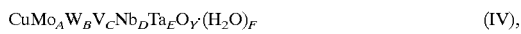

$$CuMo_AW_BV_CNb_DTa_EO_Y \cdot (H_2O)_F \qquad (IV),$$

where $1/(A+B+C+D+E)$ is from 0.7 to 1.3,

F is from 0 to 1, $B+C+D+E$ is from 0 to 1 and

Y is a number which is determined by the valency and frequency of the elements in IV other than oxygen, whose three-dimensional atomic arrangement corresponds to the structure type which is defined by the compound $CuMoO_4$-III in Russian Journal of Inorganic Chemistry 36 (7) (1991), 921, Table 1, and designated as wolframite in DE-A 4 405 514 and DE-A 4 440 891.

Among the multimetal oxides IV in turn, those having the stoichiometry V

$$CuMo_AW_BV_CO_Y \qquad (V),$$

wherein $1/(A+B+C)$ is from 0.7 to 1.3,

A, B and C are all >0, with the proviso that $B+C \leq 1$, and

Y is a number which is determined by the valency and frequency of the elements in V other than oxygen, and those having the stoichiometry VI

$$CuMo_AW_BO_Y \qquad (VI),$$

wherein $1/A+B)$ is from 0.7 to 1.3,

B/A is from 0.01 to 10, preferably from 0.01 to 1, and

Y is a number which is determined by the valency and frequency of the elements in VI other than oxygen, are noteworthy.

The preparation of multimetal oxides IV, V and VI is disclosed in DE-A 4 405 514 and DE-A 4 440 891.

Further particularly suitable multimetal oxides II are those of the general formula VII

$$CuMo_{A'}W_{B'}V_{C'}Nb_{D'}Ta_{E'}O_{Y'} \qquad (VII),$$

where $1/(A'+B'+C'+D'+E+)$ is from 0.7 to 1.3, preferably from 0.85 to 1.15, particularly preferably from 0.95 to 1.05, very particularly preferably 1, $(B'+C'+D'+E')/A'$ is from 0.01 to 10, preferably from 0.05 to 3, particularly preferably from 0.075 to 1.5, and Y' is a number which is determined by the valency and frequency of the elements in VII other than oxygen, whose structure type is the HT copper molybdate type disclosed in DE-A 19 528 646.

Among the multimetal oxides VII in turn, those in which $C'+D'+E'=O$ are preferred. A VII which is particularly recommended as multimetal oxide II is that of the composition $Mo_{10.8}W_{1.2}Cu_{12}O_{42-48}$.

Further possible multimetal oxides II are mixtures of multimetal oxides IV and VII, as likewise disclosed in DE-A 19 528 646. This applies in particular to those mixtures which contain the multimetal oxides IV and VII in intergrown form.

Before its use for the preparation of catalysts comprising multimetal oxide materials III, the mixture produced from separately preformed finely divided multimetal oxides I and II can of course also first be compressed, then milled and only thereafter brought into the desired catalyst form. As in the case of the separately preformed multimetal oxides I and II, the diameter range from >0 to 300 μm, particularly preferably 0,5 to 50 μm, very particularly preferably from 1 to 30 μm, is also recommended for the maximum particle diameter.

The particular advantage of the novel multiphase catalysts comprising multimetal oxide materials III is that the calcination conditions required for obtaining the various phases are as a rule different from one another. As a result of the principle of separate preformation, the calcination conditions of the particular phase desired can be optimally adapted.

Beyond the abovementioned uses, the multimetal oxides I are suitable very generally for improving the performance of catalytically active multimetal oxide materials, as described, for example, in DE-A 4 335 973, U.S. Pat. No. 4,035,262, DE-A 4 405 058, DE-A 4 405 059, DE-A 4 405 060, DE-A 4 405 514, DE-A 4 440 891 and DE-A 19 528 646.

For this purpose, for example, the active materials described there are mixed in finely divided form with finely divided multimetal oxides I in a simple manner and are shaped in the same way as the thorough starting mixture for the preparation of catalysts comprising multimetal oxide materials III.

The multimetal oxides I are particularly suitable as a component of the co-phases of the multiphase catalysts comprising multimetal oxide materials and disclosed in DE-A 4 405 058, DE-A 4 405 059, DE-A 4 405 060, DE-A 4 405 514 and DE-A 4 440 891. The multimetal oxides I are furthermore suitable as a component of the active phase of the multiphase catalysts of DE-A 19 528 646 which comprise multimetal oxide materials. In all these cases, multiphase catalysts which comprise multimetal oxide materials and contain phases comprising multimetal oxides I in finely divided (from >0 to 300 μm) homogenous distribution are formed. They are particularly suitable as catalysts for the catalytic gas-phase oxidations of organic compounds, which oxidations are stated in the respective cited publications.

Finally, it should be noted that the present invention permits the preparation of pure multimetal oxides I for the first time.

EXAMPLES

1) Preparation and identification of novel multimetal oxides MI1 to MI9 and comparative multimetal oxides VMI1 and VMI2

General Aspects

The novel multimetal oxides I described below all contain the elemental constituents Mo and W in the oxidation state +6. On the other hand, the oxidation state of the elemental constituent V is as a rule a distribution over its possible oxidation stage $V^{3+}$, $V^{4+}$ and $V^{5+}$. It was possible to determine this distribution by titrimetric analysis with potentiometric endpoint indication (combined platinum electrode and potentiograph from Metrohm, 9100 Herisau, Switzerland), it being necessary to effect the procedure under an inert gas atmosphere. Carrying out the titration at 80° C. facilitated the endpoint detection. In other respects, the potentiometric analysis was as follows in all cases:

In each case 0.15 g of the oxidic sample material was dissolved in a mixture of 5 ml of concentrated phosphoric acid (density $\rho$ at 20° C.=1.70 g/cm³) and 10 ml of aqueous sulfuric acid with heating (argon atmosphere), the aqueous sulfuric acid solution used in turn being a mixture of equal volumes of water and concentrated sulfuric acid ($\rho^{20}$=1.52 g/cm³) (the stated volumes relate to 20° C.). The solvent was chosen so that it did not change the possible oxidation states of V, which was checked by means of appropriate V standards.

For the analytical determination of the $V^{5+}$ content, the freshly prepared resulting solution was titrated with a 0.1 molar aqueous ammonium ferrous sulfate standard solution (($NH_4)_2Fe(SO_4)_2$). For the analytical determination of $V^{3+}$ and $V^{4+}$, a fresh solution prepared in a corresponding manner was titrated with a freshly prepared 0.02 molar aqueous potassium permanganate standard solution ($KMnO_4$), two potential jumps occurring ($V^{3+} \rightarrow V^{4+}$ and $V^{4+} \rightarrow V^{5+}$). The sum of the $V^{3+}$, $V^{4+}$ and $V^{5+}$ contents determined as described has to correspond to the total V content of the sample. This too could be determined by titrimetric analysis with potentiometric endpoint indications.

For this purpose, 0.15 g of the oxidic sample material was dissolved in a mixture of 10 ml of the abovementioned semiconcentrated aqueous sulfuric acid and 10 ml of concentrated nitric acid ($\rho^{20}$=1.52 g/cm³) with heating (argon atmosphere). Thereafter, the solution obtained was concentrated by heating with evaporation of the nitric acid and of some of the sulfuric acid used to a residual volume of about 3 ml, the total V content being converted in the oxidation state +5. After cooling, the residual volume was diluted to 50 ml and the $V^{5+}$ present was titrated potentiometrically with a 0.1 molar aqueous $(NH_4)_2Fe(SO_4)_2$ standard solution to beyond the equivalence point (endpoint).

The aqueous solution thus obtained was titrated with a freshly prepared 0.02 molar aqueous potassium permanganate standard solution, two potential jumps occurring. The first potential jump indicated the excess of $Fe^{2+}$ used, and the second potential jump gave the amount of $KMnO_4$ which was required for the oxidation of $V^{4+}$ to $V^{5+}$ and which corresponds to the total V content of the sample.

MI1: $Mo_{8.54}V_{2.47}W_{0.95}O_{33.53}$ 33.746 kg of ammonium heptamolybdate hydrate ($MoO_3$ content: 81.8% by weight, ideal composition: $(NH_4)_6Mo_7O_{24}\cdot 4H_2O$), 6.576 kg of ammonium metavanadate ($V_2O_5$ content: 76.5% by weight, ideal composition: $NH_4VO_3$), 5.764 kg of ammonium paratungstate hydrate ($WO_3$ content: 89.0% by weight, ideal composition: $(NH_4)_{10}W_{12}O_{41}\cdot 7H_2O$) and 7.033 kg of ammonium acetate ($CH_3COONH_4$ content: 97.0% by weight, ideal composition: $CH_3COONH_4$) were dissolved in the stated order in succession in 250 l of water at 90° C. while stirring. The resulting yellow to orange solution was cooled to 80° C. and spray-dried at an inlet temperature of 300° C. and an outlet temperature of 110° C.

800 g of the spray powder obtained were kneaded for 1 hour, with the addition of 250 g of water, in a kneader (type LUK 2,5 from Werner and Pfleiderer, 7000 Stuttgart, Germany) having an effective volume of 2.5 l. Of the 250 g of water, 180 g were added within the first 10 minutes of kneading and 70 g within the remaining 50 minutes of kneading. The resulting moist and clod-like kneaded product was dried for 15 hours at 110° C. and then forced through a sieve having a mesh size of 5 mm.

100 g of the resulting granules were then calcined in a horizontal rotary kiln with an isothermally heated quartz bulb volume of 1 l and a rotary speed of 12 revolutions per minute. The calcination conditions were as follows:

1st step: the granules used were continuously heated from 25 to 275° C. with 50 minutes;

2nd step: the granules used were continuously heated from 275 to 325° C. within 30 minutes;

3rd step: the granules used were kept at 325° C. for 4 hours;

4th step: the granules used were continuously heated from 325 to 400° C. within 30 minutes;

4th step: the granules used were kept at 400° C. for 10 minutes.

The external heating of the rotary kiln was then switched off and the latter was cooled by blowing surrounding air onto the outside. The granules used cooled to 25° C. within 5 hours.

During the individual calcination steps, gas mixtures which had the following compositions (standard temperature and pressure conditions (S.T.P.)=1 atm, 25° C.) flowed through the interior of the rotary kiln, parallel to the axis of rotation:

1st step, 2nd step and 3rd step: 3.6 l (S.T.P.)/h of air, 1.5 l (S.T.P.)/h of $NH_3$ and 44.9 l (S.T.P.)/h of $N_2$ (total gas flow: 50 l (S.T.P.)/h);

4th step, 5th step and cooling phase: 3.6 l (S.T.P.)/h of air and 44.9 l (S.T.P.)/h of $N_2$ (total gas flow: 48.5 l (S.T.P.)/h).

The resulting multimetal oxide powder MI1 had a black color and a specific surface area (determined according to DIN 66 131 by gas adsorption ($N_2$) according to Brunauer-Emmet-Teller (BET)) of 15.0 m²/g. More than 99% of the vanadium contained in the multimetal oxide MI1 was present as $V^{4+}$ (this determination was carried out as described above). The multimetal oxide MI1 thus had the stoichiometry $Mo_{8.54}V_{2.47}W_{0.99}O_{33.53}$.

The CuKα X-ray powder diffraction spectrum determined according to the statements in the description and evaluated after subtraction of the linear background contained the following diffraction lines in the relevant 2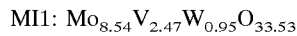 range (5 to 50°):

1. Visually resolved:

| X-ray diffraction line | 2Θ [°] | $I_A^{rel}$ [%] |
|---|---|---|
| $A^1$ | 8.4 | 5 |
| $A^2$ | 14.8 | 2 |
| $A^3$ | 22.4 | 100 |
| $A^4$ | 23.6 | 22 |
| $A^5$ | 27.2 | 41 |

-continued

| X-ray diffraction line | 2Θ [°] | $I_A^{rel}$ [%] |
|---|---|---|
| $A^6$ | — | — |
| $A^7$ | 35.2 | 14 |
| $A^8$ | — | — |
| $A^9$ | 45.5 | 19 |
| $A^{10}$ | 48.9 | 25 |

2. Mathematically resolved:

| X-ray diffraction line | 2Θ [°] | $I_F^{rel}$ [%] | FWHM [°] |
|---|---|---|---|
| $A^{1*}$ | 8.3 | 11 | 3.4 |
| $A^{2*}$ | 14.5 | 3 | 3.5 |
| $A^{3*}$ | 22.4 | 28 | 0.5 |
| $A^{4*}$ | 22.9 | 16 | 2.2 |
| $A^{5*}$ | 27.1 | 100 | 4.4 |
| $A^{6*}$ | 31.5 | 36 | 5.7 |
| $A^{7*}$ | 35.3 | 40 | 4.8 |
| $A^{8*}$ | — | — | — |
| $A^{9*}$ | 45.5 | 9 | 0.9 |
| $A^{10*}$ | 48.8 | 33 | 2.3 |

The experimentally determined CuKα X-ray powder diffraction spectrum reflecting the three-dimensional atomic arrangement of the multimetal oxide MI1 is shown in FIG. 1 (ordinate: intensity, stated as absolute counting rate; abscissa: 2Θ range from 5 to 65°).

Furthermore, FIG. 1 shows the linear background to be subtracted for the evaluation (the connecting line between A(2Θ=5°) and A(2Θ=65°)) and the position of the individual diffraction lines $A^i$. The points of contact between base line and X-ray diffraction spectrum divide the latter in a natural manner into the two 2Θ ranges from 5 to 43° and from 43 to 65°.

Figure 2:
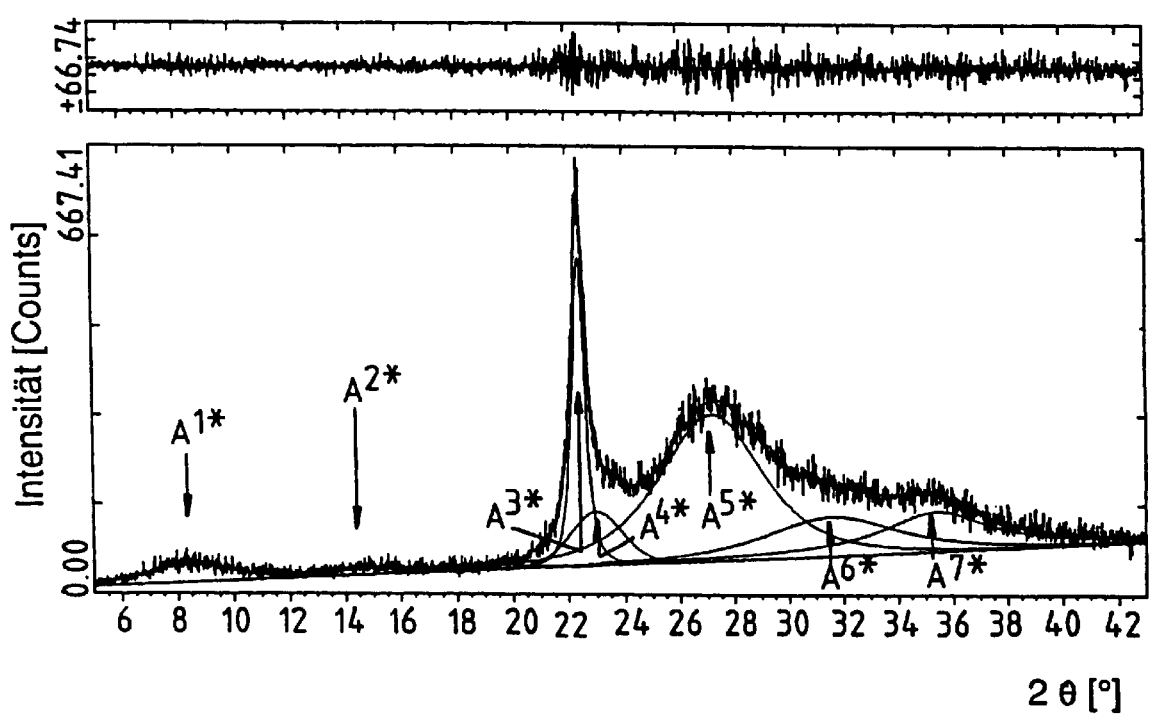
FIGS. 2 and 3 are enlargements of portions of the X-ray powder diffraction pattern shown in FIG. 1.

FIG. 2 shows the 2Θ range from 5 to 43° of the CuKα X-ray powder diffraction spectrum of the multimetal oxide MI1 on a larger scale. Furthermore, FIG. 2 shows the result (including the background line) of the mathematical fit and resolution carried out in accordance with the description for this range (PROFILE, Pearson VII profile function, fixed background). The superposition of mathematically generated diffraction lines $A^{i*}$ gives the fit to the experimental envelope.

Figure 3:
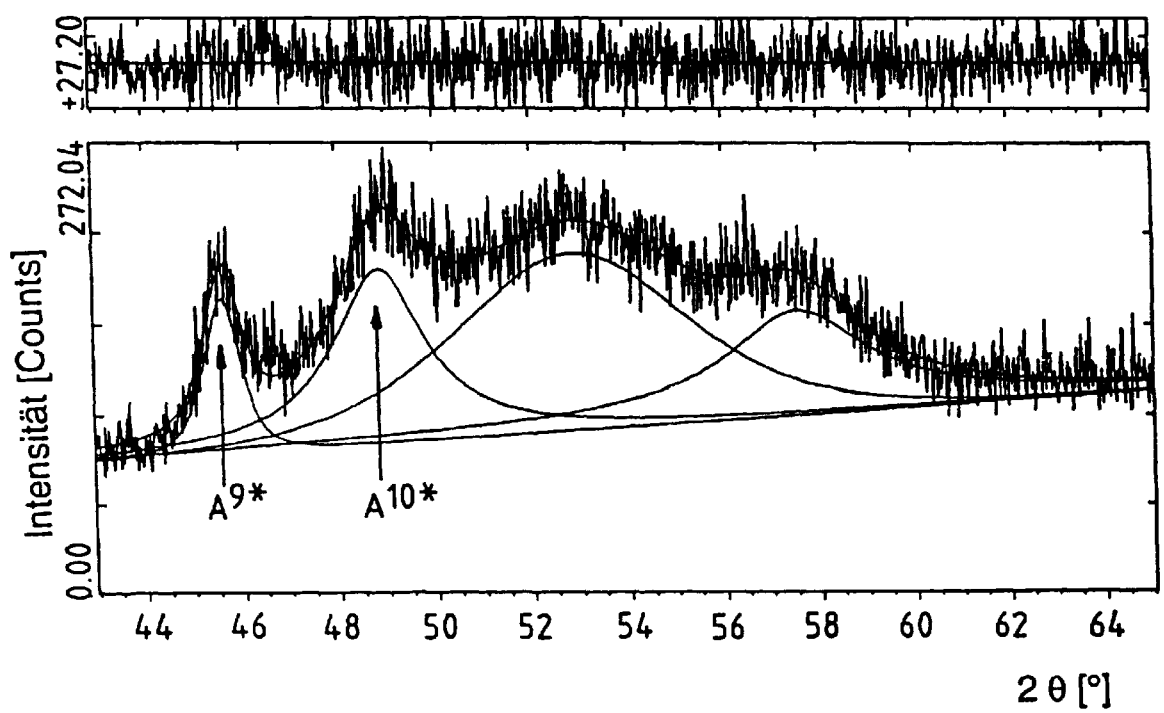

In a corresponding manner, FIG. 3 shows the 2Θ range from 43 to 65° on a larger scale and the resolution performed for this range, including the linear background line.

The rectangular section appearing above the actual X-ray diffraction spectrum in FIGS. 2 and 3 shows in each case the difference between the experimental envelope of the X-ray powder diffraction spectrum and its mathematical fit. This difference is a measure of the quality of the fit.

MI2: $Mo_{8.54}V_{2.47}W_{0.99}O_{33.53}$

Granules were produced as for MI1. 400 g of the granules were calcined in a calcination furnace operating according to the principle of a jet reactor. The granules used were present as a 5 cm high bed on a wire net through which a gas mixture flowed from below. The volume of the furnace was 3 l, and the circulation ratio [(circulated gas mixture volume flow): (freshly added gas mixture volume flow)] was chosen to be 20. The granules used were first continuously heated from 25 to 325° C. in the course of 1 hour in the stated furnace. The granules used were then kept at 325° C. for 4 hours. At the beginning of the calcination, the gas mixture flowing through was composed of 120 l (S.T.P.)/h of $N_2$, 10 l (S.T.P.)/h of air and 3.3 l (S.T.P.)/h of $NH_3$. Finally, the granules used were heated from 325 to 400° C. within 20 minutes and then kept at 400° C. for a further hour. In this final phase, a gas mixture comprising 120 l (S.T.P.)/h of $N_2$ and 10 l (S.T.P.)/h of air flowed through. Cooling to room temperature was effected by cutting off the heat supply.

The resulting multimetal oxide powder MI2 was identical to the multimetal oxide MI1 with respect to the $V^{5+,4+,3+}$ analysis and with respect to its CuKα X-ray powder diffraction spectrum.

MI3: $Mo_{8.35}V_{2.60}W_{1.05}O_{33.40}$ 852.78 g of ammonium heptamolybdate hydrate ($MoO_3$ content: 81.0% by weight, ideal composition: $(NH_4)_6Mo_7O_{24} \cdot 4 H_2O$), 177.14 g of ammonium metavanadate ($V_2O_5$ content: 77.0% by weight, ideal composition: $NH_4VO_3$) and 156.29 g of ammonium paratungstate hydrate ($WO_3$ content: 89.0% by weight, ideal composition: $(NH_4)_{10}W_{12}O_{41} \cdot 7 H_2O$) were dissolved in the stated order in succession in 5 l of water at 95° C. The yellow to orange solution obtained was cooled to 80° C. and spray-dried at an inlet temperature of 300° C. and an outlet temperature of 110° C. 100 g of the spray-dried powder were then calcined in a horizontal rotary kiln with an isothermally heated quartz bulb volume of 1 l and a rotary speed of 12 revolutions per minute under the conditions defined below. The powder used was continuously heated from 25 to 275° C. in a first step within 50 minutes, continuously heated from 275 to 325° C. within 30 minutes in a second step immediately after the first step, kept at 325° C. for 4 hours in a third step immediately after the second step and heated from 325 to 400° C. within 3.5 hours in a fourth step immediately after the third step. During the first three steps, a gas mixture consisting of 9.6 l (S.T.P.)/h of air, 3 l (S.T.P.)/h of $NH_3$ and 87.4 l (S.T.P.)/h of $N_2$ (total gas flows: 100 l (S.T.P.)/h) flowed through the quartz bulb. During the fourth step, a gas mixture consisting of 9.6 l (S.T.P.)/h of air and 87.4 l (S.T.P.)/h of $NH_2$ flowed through the quartz bulb (total gas flow=97 l (S.T.P.)/h). After the end of the fourth step, the external heating of the rotary kiln was switched off and cooling was effected from the outside by blowing on air. The powder used cooled to 25° C. within 5 hours under the gas mixture comprising 9.6 l (S.T.P.)/h of air and 87.4 l (S.T.P.)/h of $NH_2$ and flowing unchanged through the quartz bulb.

Figure 4:
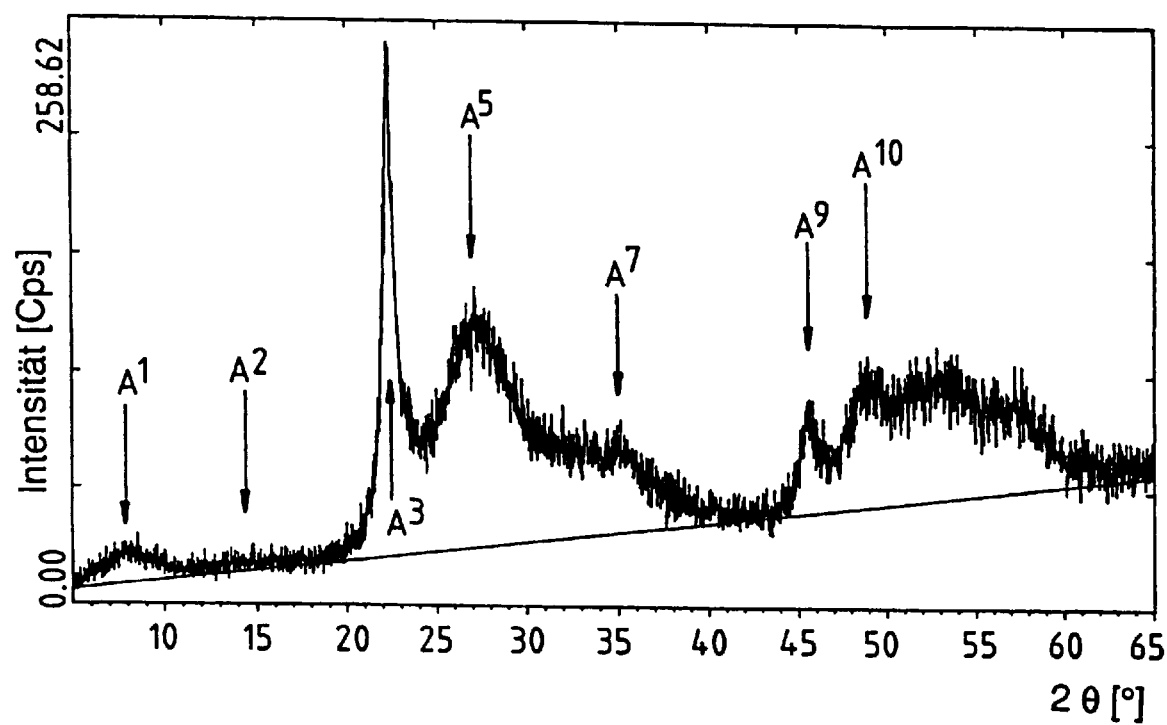
FIGS. 4–6 shows the Cu Kα X-ray powder diffraction patterns of another multimetal oxide of the present invention.
Figure 5:
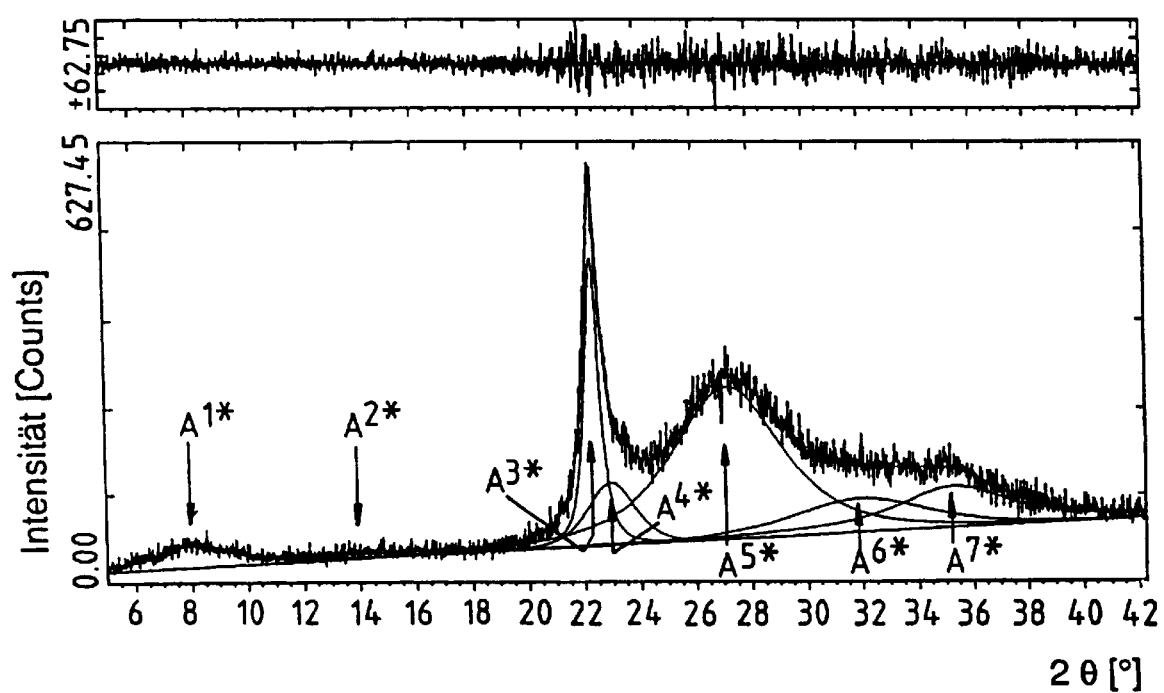
Figure 6:
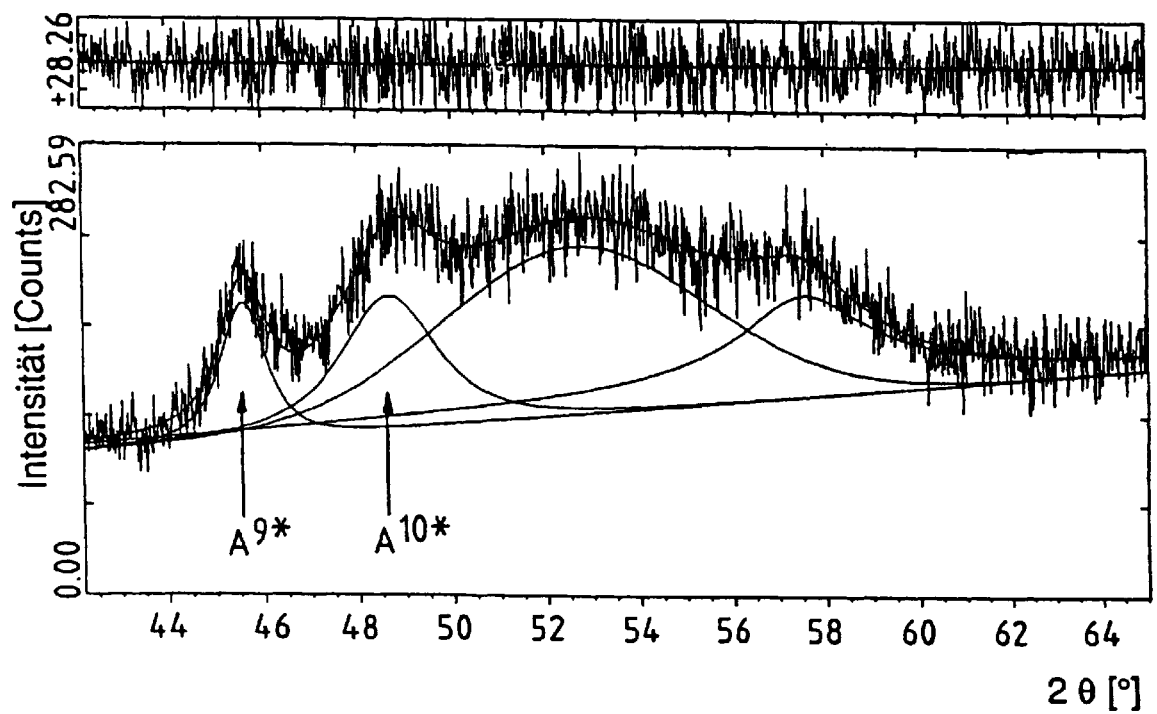

The resulting multimetal oxide powder MI3 had a black color and a specific surface area (DIN 66131) of 0.5 m²/g. More than 99% of the vanadium contained in the multimetal oxide MI3 was present as $V^{4+}$. The multimetal oxide MI3 thus had the stoichiometry $Mo_{8.35}V_{2.60}W_{1.05}O_{33.40}$. The associated CuKα X-ray powder diffraction spectrum is shown in FIGS. 4 to 6. It shows the three-dimensional atomic arrangement in common with MI1. Its evaluation, carried out as for MI1, gave the following diffraction lines in the relevant 2Θ range.

1. Visually resolved:

| X-ray diffraction line | 2Θ [°] | $I_A^{rel}$ [%] |
|---|---|---|
| $A^1$ | 7.9 | 7 |
| $A^2$ | 14.7 | scarcely detectable |

-continued

| X-ray diffraction line | 2Θ [°] | $I_A^{rel}$ [%] |
|---|---|---|
| $A^3$ | 22.3 | 100 |
| $A^4$ | — | — |
| $A^5$ | 27.1 | 45 |
| $A^6$ | — | — |
| $A^7$ | 35.0 | 17 |
| $A^8$ | — | — |
| $A^9$ | 45.5 | 20 |
| $A^{10}$ | 49.0 | 25 |

2. Mathematically resolved:

| X-ray diffraction line | 2Θ [°] | $I_F^{rel}$ [%] | FWHM [°] |
|---|---|---|---|
| $A^{1*}$ | 8.0 | 12 | 3.4 |
| $A^{2*}$ | 14.0 | 2 | 3.1 |
| $A^{3*}$ | 22.3 | 28 | 0.6 |
| $A^{4*}$ | 22.9 | 16 | 2.0 |
| $A^{5*}$ | 27.1 | 100 | 4.6 |
| $A^{6*}$ | 31.9 | 25 | 5.7 |
| $A^{7*}$ | 35.2 | 34 | 5.0 |
| $A^{8*}$ | — | — | — |
| $A^{9*}$ | 45.5 | 10 | 1.0 |
| $A^{10*}$ | 48.6 | 20 | 2.4 |

MI4: $Mo_{8.35}V_{2.60}W_{1.05}O_{33.40}$

A spray-dried powder was produced as for MI3. 60 g of the spray-dried powder were then calcined in a horizontal rotary kiln with an isothermally heated quartz bulb volume of 1 l and a rotary speed of 12 revolutions per minute under the conditions defined below. The powder used was heated from 25 to 275° C. within 50 minutes in a first step, continuously heated from 275 to 325° C. within 30 minutes in a second step immediately after the first step, kept at 325° C. for 3 hours in a third step immediately after the second step and heated from 325 to 400° C. within 90 minutes in a fourth step immediately after the third step and then kept at 400° C. for 10 minutes. During the first 3 steps, a gas mixture consisting of 4.8 l (S.T.P.)/h of air, 1.5 l (S.T.P.)/h of $NH_3$ and 43.7 l (S.T.P.)/h of $NH_2$ flowed through the quartz bulb (total gas flow: 50 l (S.T.P.)/h). During the fourth and fifth steps, a gas mixture consisting of 4.8 l (S.T.P.)/h of air and 43.7 l (S.T.P.)/h of $NH_2$ flowed through the quartz bulb (total gas flow: 48.5 l (S.T.P.)/h). After the end of the fifth step, the external heating of the rotary kiln was switched off and cooling was effected by blowing on air from the outside. The powder used cooled to 25° C. within 5 hours under the gas mixture comprising 4.8 l (S.T.P.)/h of air and 43.7 l (S.T.P.)/h of $NH_2$ and flowing unchanged through the quartz bulb.

Figure 7:
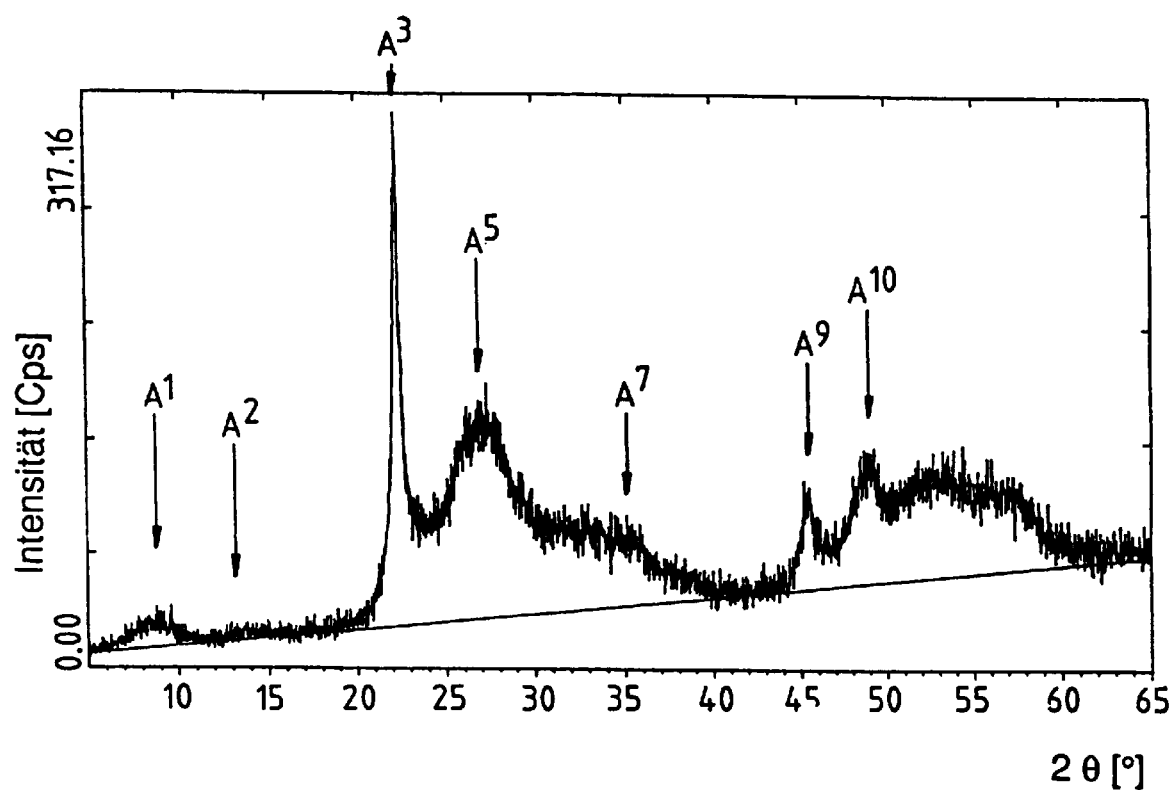
FIGS. 7–9 show the Cu Kα X-ray powder diffraction pattern of another multimetal oxide of the present invention.
Figure 8:
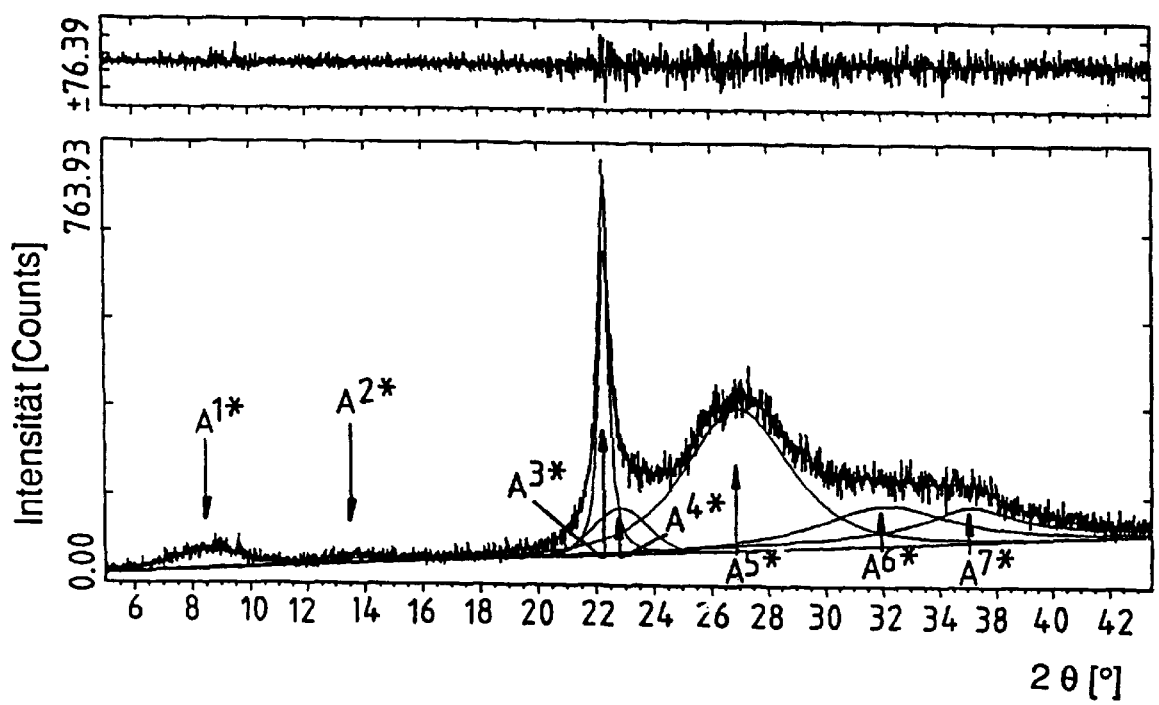
Figure 9:
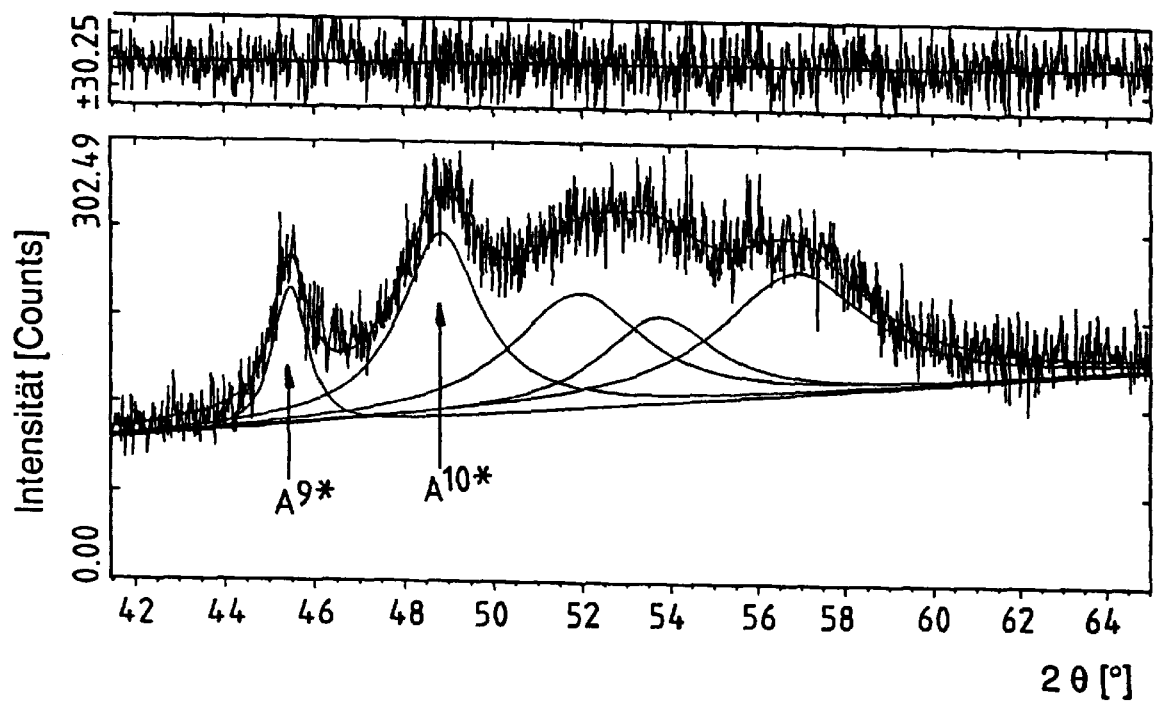

The resulting multimetal oxide powder MI4 was identical to the multimetal oxide MI3 with respect to the $V^{5+}$, $V^{4+}$ and $V^{3+}$ analysis and with respect to its CuKα X-ray powder diffraction spectrum. The quantitative evaluation of the X-ray diffraction spectrum carried out as described (shown in FIGS. 7 to 9) gave the following in the relevant 2Θ range:

1. Visually resolved:

| X-ray diffraction line | 2Θ [°] | $I_A^{rel}$ [%] |
|---|---|---|
| $A^1$ | 8.9 | 5 |
| $A^2$ | 13.8 | still just detectable |
| $A^3$ | 22.3 | 100 |
| $A^4$ | — | — |
| $A^5$ | 27.0 | 40 |
| $A^6$ | — | — |
| $A^7$ | 35.3 | still just detectable |
| $A^8$ | — | — |
| $A^9$ | 45.3 | 18 |
| $A^{10}$ | 49.0 | 24 |

2. Mathematically resolved:

| X-ray diffraction line | 2Θ [°] | $I_F^{rel}$ [%] | FWHM [°] |
|---|---|---|---|
| $A^{1*}$ | 8.5 | 8 | 2.8 |
| $A^{2*}$ | 13.7 | 2 | 2.1 |
| $A^{3*}$ | 22.2 | 26 | 0.4 |
| $A^{4*}$ | 22.8 | 15 | 2.2 |
| $A^{5*}$ | 26.9 | 100 | 4.3 |
| $A^{6*}$ | 32.0 | 42 | 5.6 |
| $A^{7*}$ | 35.1 | 61 | 4.7 |
| $A^{8*}$ | — | — | — |
| $A^{9*}$ | 45.4 | 9 | 0.9 |
| $A^{10*}$ | 48.8 | 34 | 2.2 |

MI5: $Mo_{8.54}V_{2.47}W_{0.99}O_{33.01}$ 800 g of the spray powder produced for the preparation of MI1 were kneaded in a kneader (type LUK 2, 5 from Werner and Pfleiderer, 7000 Stuttgart, Germany) having an effective volume of 2.5 l with the addition of 80 g of acetic acid (100% strength) and 200 g of water for 1 hour. The 80 g of acetic acid and 80 g of water were added during the first 10 minutes of kneading. The remaining 120 g of water were added during the remaining 50 minutes of kneading. The resulting moist and clod-like kneaded product was dried for 15 hours at 110° C. and then forced through a sieve having a mesh size of 5 mm. 100 g of the resulting granules were then calcined in a horizontal rotary kiln as described for MI1.

Figure 10:
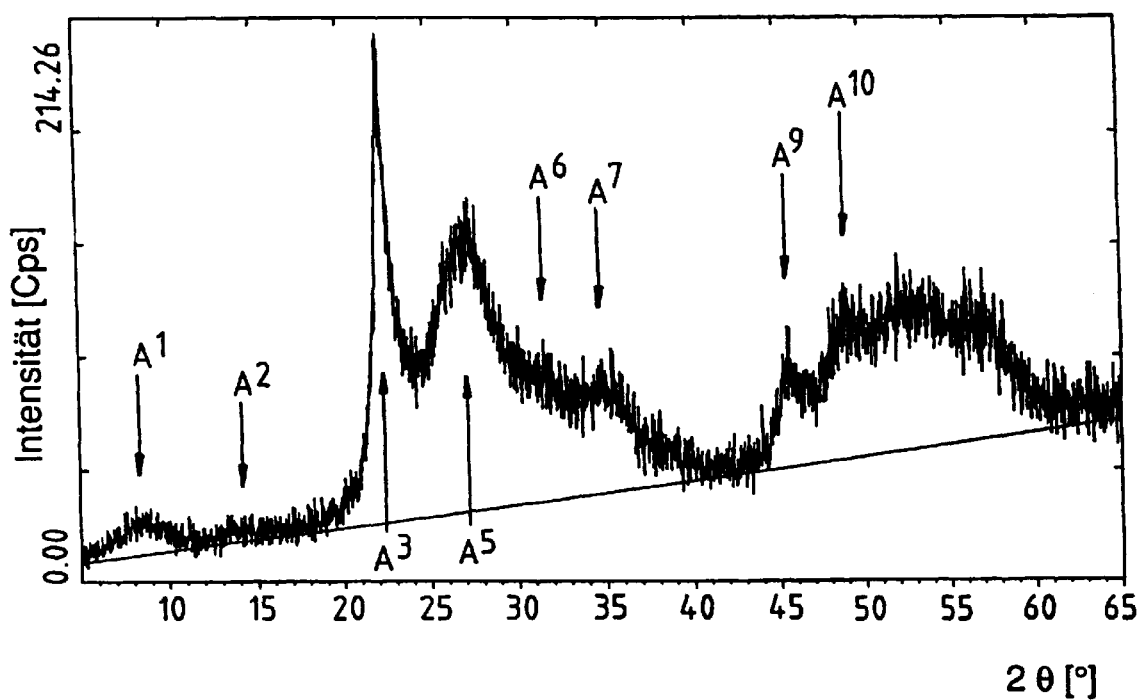
FIGS. 10–12 show the Cu Kα X-ray powder diffraction pattern of another multimetal oxide of the present invention.
Figure 11:
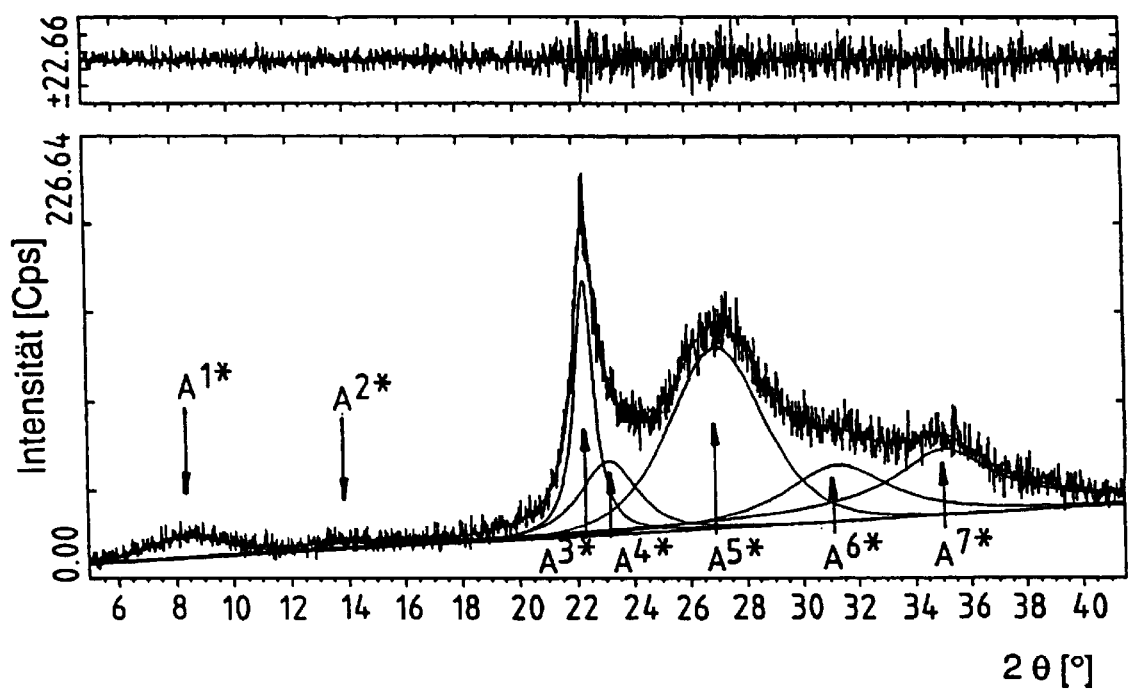
Figure 12:
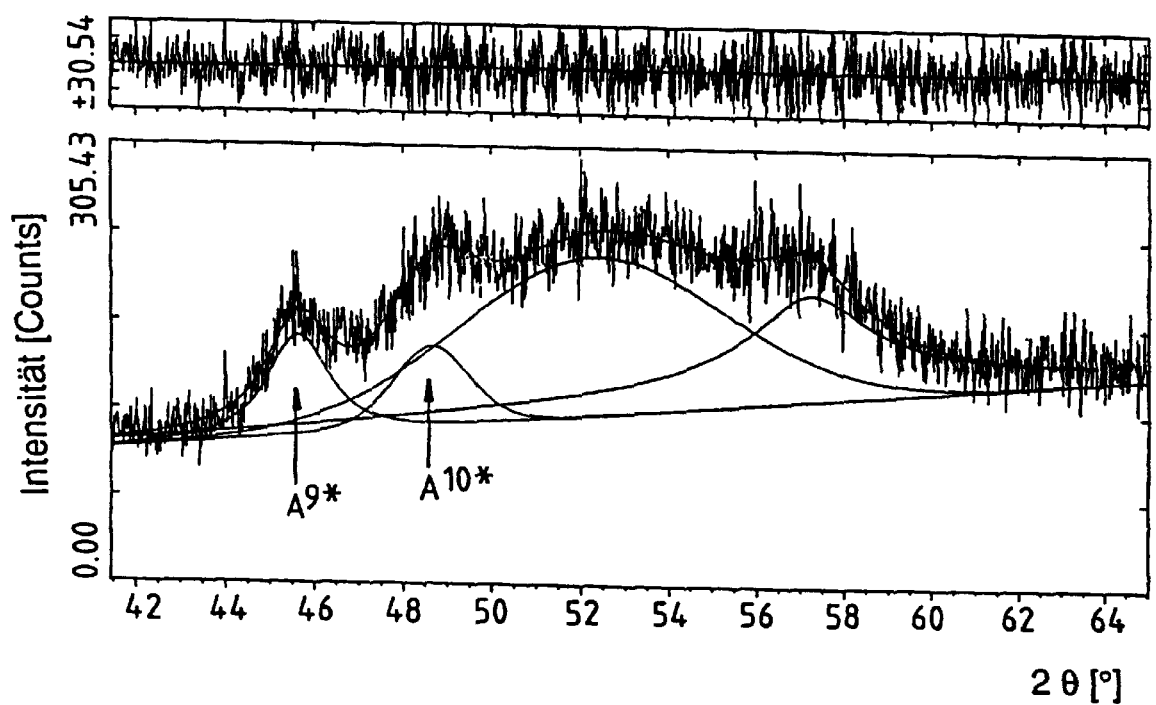

The resulting multimetal oxide powder MI5 had a black color and a specific surface area (DIN 66131) of 16.0 m²/g. 42% of the vanadium contained in the multimetal oxide MI5 were present as $V^{3+}$ and 58% as $V^{4+}$. In contrast to the multimetal oxide MI1, the multimetal oxides MI5 thus had the stoichiometry $Mo_{8.54}V_{2.47}W_{0.99}O_{33.01}$. The CuKα X-ray powder diffraction spectrum determined and evaluated as for the multimetal oxide MI1 nevertheless reflected the same three-dimensional atomic arrangement for the multimetal oxide MI5 as for the multimetal oxide MI1 (cf. FIGS. 10 to 12). The diffraction lines determined in the relevant 2Θ range are:

1. Visually resolved:

| X-ray diffraction line | 2Θ [°] | $I_A^{rel}$ [%] |
|---|---|---|
| $A^1$ | 8.6 | 8 |
| $A^2$ | 14.3 | 3 |
| $A^3$ | 22.3 | 100 |
| $A^4$ | — | — |
| $A^5$ | 27.2 | 59 |
| $A^6$ | 31.6 | 26 |
| $A^7$ | 34.8 | 24 |
| $A^8$ | — | — |
| $A^9$ | 45.5 | 24 |
| $A^{10}$ | 49.0 | 31 |

2. Mathematically resolved:

| X-ray diffraction line | 2Θ [°] | $I_F^{rel}$ [%] | FWHM [°] |
|---|---|---|---|
| $A^{1*}$ | 8.4 | 10 | 3.1 |
| $A^{2*}$ | 13.9 | 2 | 2.0 |
| $A^{3*}$ | 22.3 | 38 | 0.8 |
| $A^{4*}$ | 23.1 | 27 | 2.4 |
| $A^{5*}$ | 26.9 | 100 | 4.0 |
| $A^{6*}$ | 31.2 | 42 | 4.4 |
| $A^{7*}$ | 35.0 | 85 | 4.6 |
| $A^{8*}$ | — | — | — |
| $A^{9*}$ | 45.6 | 15 | 1.6 |
| $A^{10*}$ | 48.6 | 12 | 2.0 |

VMI1: $Mo_{8.54}V_{2.47}W_{0.99}O_{34.18}$ 100 g of the granules obtained for the preparation of MI5 by kneading spray powder with water and acetic acid were calcined, as described in Example MI1, in a horizontal rotary kiln. Instead of the various gas mixtures, however, a corresponding amount of pure air flowed through the rotary kiln in each case.

Figure 13:
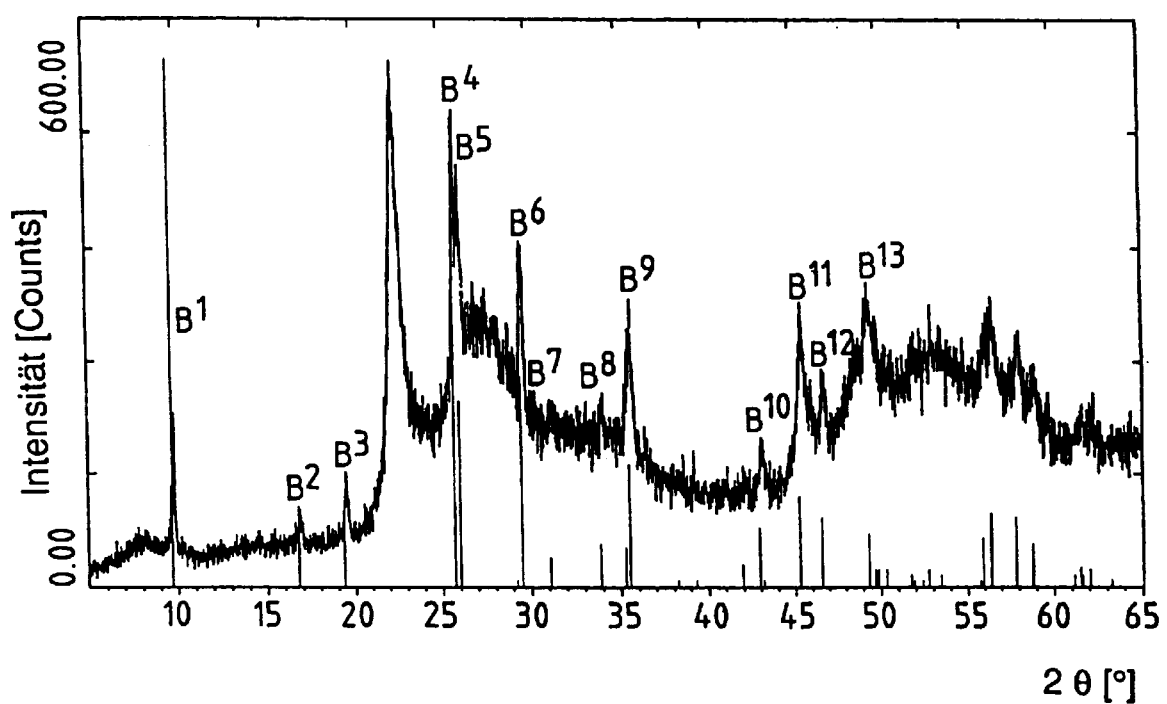
FIG. 13 shows the Cu Kα X-ray powder diffraction pattern of a comparative example.

The resulting multimetal oxide powder VMI1 had a black color and a specific surface area (DIN 66131) of 16.2 m²/g. 47% of the vanadium contained in the multimetal oxide VMI1 were present as $V^{4+}$ and 53% as $V^{5+}$. In contrast to the multimetal oxides MI1 and MI5, the multimetal oxide VMI1 thus had the stoichiometry $Mo_{8.54}V_{2.47}W_{0.99}O_{34.18}$. The associated CuKα X-ray powder diffraction spectrum is shown in FIG. 13. It is evidently different from that of the multimetal oxide MI1 and, in the 2Θ range from 5 to 50°, contains, for example, the following intense diffraction lines (having a relatively small half-width).

Visually resolved:

| X-ray diffraction line | 2Θ [°] | $I_A^{rel}$ [%] | FWHM [°] |
|---|---|---|---|
| $B^1$ | 9.7 | 32 | 0.15 |
| $B^2$ | 16.8 | 7 | 0.18 |
| $B^3$ | 19.4 | 15 | 0.23 |
| $B^4$ | 25.8 | 91 | 0.19 |
| $B^5$ | 26.1 | 78 | 0.23 |
| $B^6$ | 29.5 | 62 | 0.21 |
| $B^7$ | 31.2 | 24 | 0.45 |
| $B^8$ | 34.0 | 26 | 0.17 |
| $B^9$ | 35.7 | 44 | 0.36 |
| $B^{10}$ | 43.1 | 12 | 0.25 |

-continued

| X-ray diffraction line | 2Θ [°] | $I_A^{rel}$ [%] | FWHM [°] |
|---|---|---|---|
| $B^{11}$ | 45.4 | 39 | 0.63 |
| $B^{12}$ | 46.7 | 26 | 0.45 |
| $B^{13}$ | 49.4 | 41 | 1.18 |

This means that the three-dimensional atomic arrangement of the multimetal oxide VMI1 does not correspond to that of the multimetal oxide MI1 or MI5.

MI6: $Mo_{9.6}V_{2.4}O_{34.37}$ 239.74 g of oxalic acid dihydrate (ideal composition: $H_2C_2O_4 \cdot 2 H_2O$, $H_2C_2O_4$ content: 71.4% by weight) were dissolved in 4 l of water at 80° C. in a first vessel. Thereafter, 90.22 g of ammonium polyvanadate ($V_2O_5$ content: 88.2% by weight, ideal composition: $(NH_4)_2V_6O_{16}$) were dissolved in the resulting aqueous solution while stirring and while maintaining the temperature of 80° C., a deep blue aqueous solution A being formed. The ammonium polyvanadate was added in small portions in the course of 15 minutes in order to prevent the reaction batch from frothing over. In a second vessel, 619.60 g of ammonium heptamolybdate hydrate ($MoO_3$ content: 81.3% by weight, ideal composition: $(NH_4)_6Mo_7O_{24} \times 4 H_2O$) were dissolved in 4 l of water at 80° C. while stirring (solution B). Thereafter, solution B was continuously stirred into solution A at 80° C. with 15 minutes. The resulting deep blue aqueous solution was stirred for a further 15 hours at 80° C. and then spray-dried (inlet temperature: 310° C., outlet temperature: 110° C.).

100 g of the spray-dried powder were calcined in a horizontal rotary kiln with an isothermally heated quartz bulb volume of 1 l and a rotary speed of 12 revolutions per minute under the conditions below. The powder used was continuously heated from 25 to 275° C. within 50 minutes in a first step, continuously heated from 275 to 325° C. within 35 minutes in a second step immediately after the first step and kept at 325° C. for 4 hours in a third step immediately thereafter. Directly afterward, the powder used was heated from 325 to 400° C. within 35 minutes in a fourth step and kept at 400° C. for 10 minutes in a fifth step immediately thereafter. The external heating of the rotary kiln was then switched off and the quartz bulb was cooled by blowing on air from the outside. The powder used cooled to room temperature (25° C.) within 5 hours. During the entire calcination time (including the cooling phase), 50 l (S.T.P.)/h of air flowed through the quartz bulb.

The resulting multimetal oxide powder MI6 had a black color and a specific surface area (DIN 66131) of 6.6 m²/g. 36% of the vanadium contained in the multimetal oxide MI6 were present as $V^{4+}$ and 64% as $V^{5+}$. The multimetal oxide MI6 thus had the stoichiometry $Mo_{9.6}V_{2.4}O_{34.37}$.

Figure 14:
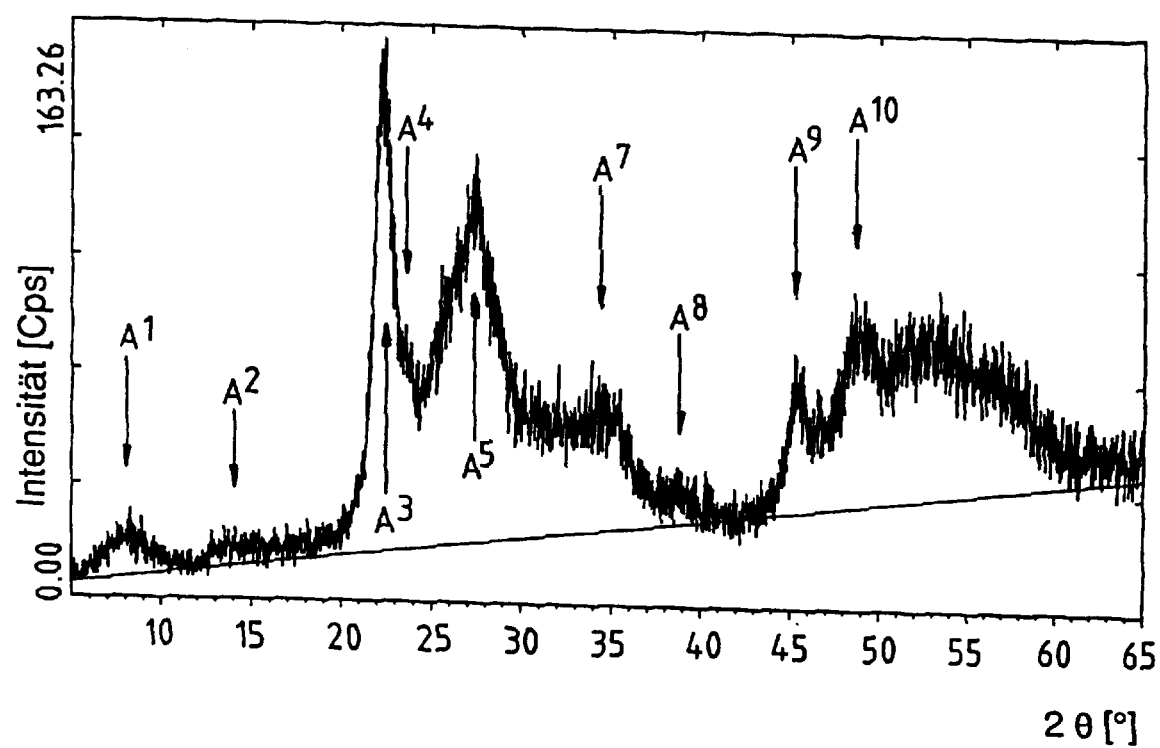
FIG. 14 shows the Cu Kα X-ray powder diffraction pattern of another multimetal oxide of the present invention.

The visual appearance of the associated CuKα X-ray powder diffraction spectrum corresponded to that of MI1 (cf. FIG. 14) and had the three-dimensional atomic arrangement in common with MI1. Its valuation carried out as for MI1 gave the following diffraction lines in the relevant 2Θ range:

1. Visually resolved:

| X-ray diffraction line | 2Θ [°] | $I_A^{rel}$ [%] |
|---|---|---|
| $A^1$ | 8.0 | 9 |
| $A^2$ | 14.1 | 4 |
| $A^3$ | 22.3 | 100 |
| $A^4$ | 23.5 | 40 |
| $A^5$ | 27.4 | 74 |
| $A^6$ | — | — |
| $A^7$ | 34.5 | 26 |
| $A^8$ | 38.7 | 12 |
| $A^9$ | 45.4 | 27 |
| $A^{10}$ | 48.9 | 38 |

2. Mathematically resolved:

| X-ray diffraction line | 2Θ [°] | $I_F^{rel}$ [%] | FWHM [°] |
|---|---|---|---|
| $A^{1*}$ | 8.0 | 5 | 2.7 |
| $A^{2*}$ | 13.8 | 2 | 2.3 |
| $A^{3*}$ | 22.2 | 19 | 0.9 |
| $A^{4*}$ | 23.0 | 23 | 2.6 |
| $A^{5*}$ | 27.3 | 100 | 3.0 |
| $A^{6*}$ | 32.8 | 51 | 7.8 |
| $A^{7*}$ | 34.8 | 4 | 1.8 |
| $A^{8*}$ | — | — | — |
| $A^{9*}$ | 45.3 | 8 | 1.3 |
| $A^{10*}$ | 48.6 | 16 | 2.3 |

MI7: $Mo_{9.6}V_{2.4}O_{34.13}$ 100 g of the spray-dried powder prepared for MI6 were calcined in a horizontal rotary kiln with an isothermally heated quartz bulb volume of 1 l and a rotary speed of 12 revolutions per minute under the conditions below. The powder used was heated from 25 to 275° C. within 50 minutes in a first step, continuously heated from 275 to 300° C. within 25 minutes in a second immediately after the first step and kept at 300° C. for 4 hours in a third step immediately thereafter. The external heating of the rotary kiln was then switched off and the bulb was cooled by blowing on air from the outside. The powder used cooled to room temperature (25° C.) within 3 hours. During the entire calcination time (including the cooling phase), 50 l (S.T.P.)/h of air flowed through the quartz bulb.

The resulting multimetal oxide powder MI7 had a black color and a specific surface area (DIN 66131) of 5.7 m²/g. 56% of the vanadium contained in the multimetal oxide MI6 were present as $V^{4+}$ and 44% as $V^{5+}$. The multimetal oxide MI7 thus had the stoichiometry $Mo_{9.6}V_{2.4}O_{34.13}$.

Figure 15:
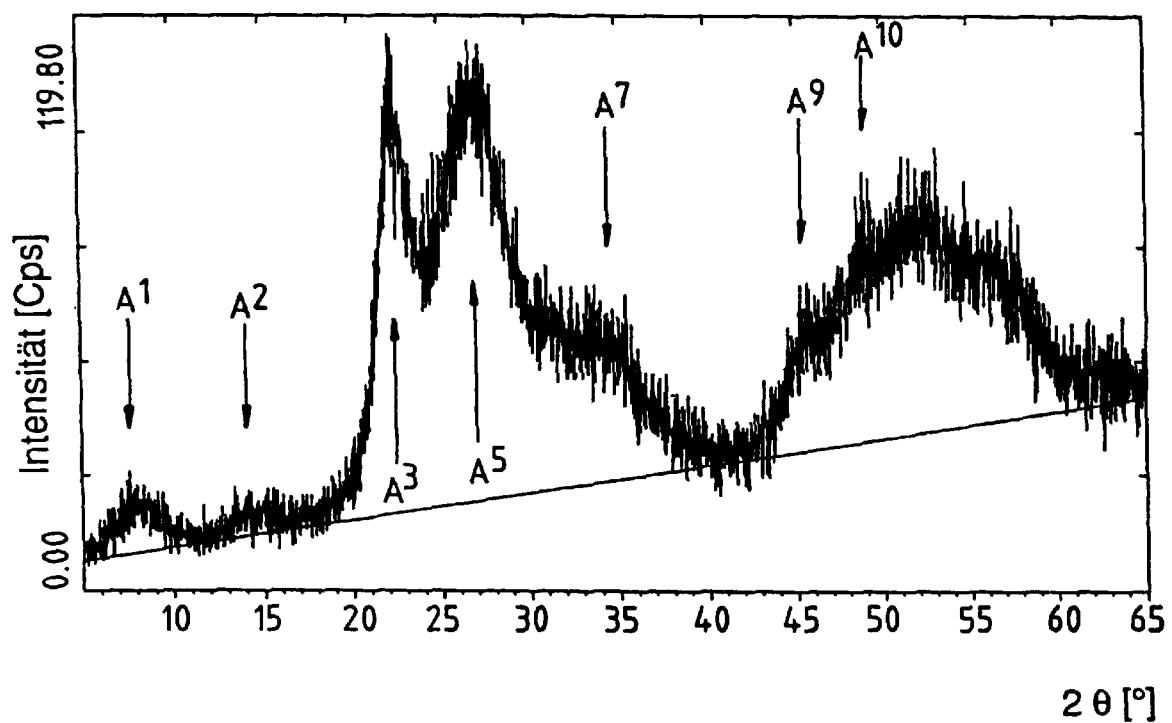
FIG. 15 shows the Cu Kα X-ray powder diffraction pattern of another multimetal oxide of the present invention.

The visual appearance of the associated CuKα X-ray powder diffraction spectrum corresponded to that of MI1 (cf. FIG. 15) and had the three-dimensional atomic arrangement in common with MI1. Its evaluation carried out as for MI1 gave the following diffraction lines in the relevant 2Θ range:

1. Visually resolved:

| X-ray diffraction line | 2Θ [°] | $I_A^{rel}$ [%] |
|---|---|---|
| $A^1$ | 7.9 | 10 |
| $A^2$ | 14.2 | 5 |
| $A^3$ | 22.3 | 100 |
| $A^4$ | — | — |
| $A^5$ | 27.1 | 94 |
| $A^6$ | — | — |
| $A^7$ | 34.7 | 30 |
| $A^8$ | — | — |
| $A^9$ | 45.6 | 29 |
| $A^{10}$ | 49.0 | 48 |

2. Mathematically resolved:

| X-ray diffraction line | 2Θ [°] | $I_F^{rel}$ [%] | FWHM [°] |
|---|---|---|---|
| $A^{1*}$ | 7.9 | 7 | 3.1 |
| $A^{2*}$ | 14.3 | 4 | 3.0 |
| $A^{3*}$ | 22.3 | 39 | 2.0 |
| $A^{4*}$ | — | — | — |
| $A^{5*}$ | 26.8 | 100 | 4.8 |
| $A^{6*}$ | 31.3 | 25 | 2.9 |
| $A^{7*}$ | 34.2 | 53 | 5.5 |
| $A^{8*}$ | — | — | — |
| $A^{9*}$ | 45.4 | 8 | 2.2 |
| $A^{10*}$ | 48.6 | 29 | 3.9 |

MI8: $Mo_{9.0}V_{3.0}O_{33.72}$ 306.86 g of oxalic acid dihydrate (ideal composition: $H_2C_2O_4 \cdot 2\ H_2O$, $H_2C_2O_4$ content: 71.4% by weight) were dissolved in 4 l of water at 80° C. in a first vessel. Thereafter, 115.48 g of ammonium polyvanadate ($V_2O_5$ content: 88.2% by weight, ideal composition: $(NH_4)_2V_6O_{16}$) were dissolved in the clear aqueous solution while stirring and while maintaining the temperature of 80° C., a deep blue aqueous solution being formed (solution A). The ammonium polyvanadate was added in small portions in the course of 15 minutes in order to prevent the reaction batch from frothing over. In a second vessel, 594.82 g of ammonium heptamolybdate hydrate ($MoO_3$ content: 81.3% by weight, ideal composition: $(NH_4)_6Mo_7O_{24} \cdot 4\ H_2O$) were dissolved in 4 l of water at 80° C. while stirring (solution B). Thereafter, solution B was continuously stirred into solution A at 80° C. within 15 minutes. The resulting deep blue aqueous solution was stirred for a further 15 hours at 80° C. and then spray-dried (inlet temperature: 310° C., outlet temperature: 110° C.).

100 g of the spray-dried powder were calcined in a horizontal rotary kiln with an isothermally heated quartz bulb volume of 1 l and a rotary speed of 12 revolutions per minute, as described for MI7, in an air stream.

Figure 16:
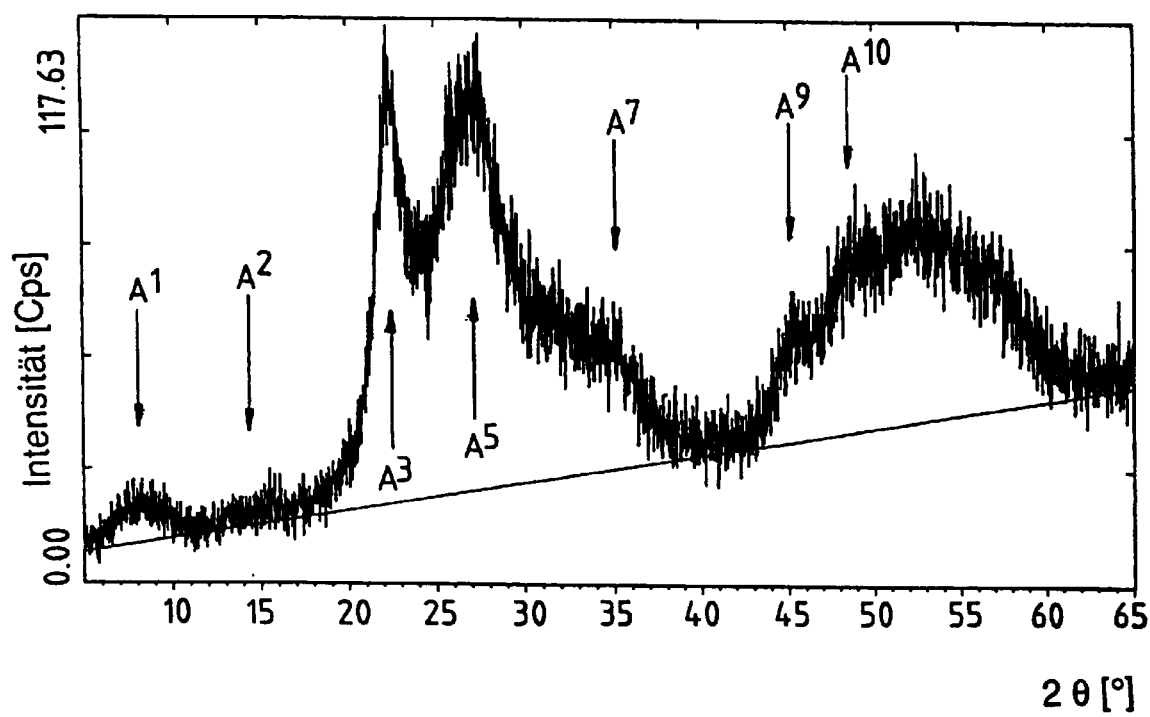
FIG. 16 shows the Cu Kα X-ray powder diffraction pattern of another multimetal oxide of the present invention.

The resulting multimetal oxide powder MI8 was black and had a specific surface area (DIN 66131) of 5, 3 m²/g. 52% of the vanadium contained in the multimetal oxide MI8 were present as $V^{4+}$ and 48% as $V^{5+}$. The multimetal oxide MI8 thus had the stoichiometry $Mo_{9.0}V_{3.0}O_{33.72}$. The visual appearance of the associated CuKα X-ray powder diffraction spectrum corresponded to that of MI1 (cf. FIG. 16) and accordingly had a three-dimensional atomic arrangement in common with MI1. Its evaluation carried out as for MI1 gave the following diffraction lines in the relevant 2Θ range:

1. Visually resolved:

| X-ray diffraction line | 2Θ [°] | $I_A^{rel}$ [%] |
|---|---|---|
| $A^1$ | 8.3 | 9 |
| $A^2$ | 14.6 | 3 |
| $A^3$ | 22.3 | 100 |
| $A^4$ | — | — |
| $A^5$ | 27.0 | 95 |
| $A^6$ | — | — |
| $A^7$ | 35.0 | 29 |
| $A^8$ | — | — |
| $A^9$ | 45.2 | 31 |
| $A^{10}$ | 48.6 | 41 |

2. Mathematically resolved:

| X-ray diffraction line | 2Θ [°] | $I_F^{rel}$ [%] | FWHM [°] |
|---|---|---|---|
| $A^{1*}$ | 8.0 | 5 | 3.1 |
| $A^{2*}$ | — | — | — |
| $A^{3*}$ | 22.3 | 24 | 1.8 |
| $A^{4*}$ | 23.9 | .11 | 1.1 |
| $A^{5*}$ | 26.9 | 100 | 5.1 |
| $A^{6*}$ | 31.9 | 11 | 3.4 |
| $A^{7*}$ | 34.9 | 26 | 4.1 |
| $A^{8*}$ | — | — | — |
| $A^{9*}$ | 45.2 | 8 | 2.3 |
| $A^{10*}$ | 48.3 | 13 | 3.0 |

MI9: $Mo_{9.0}V_{3.0}O_{34.04}$ 100 g of the spray-dried powder prepared for MI8 were calcined in a horizontal rotary kiln with an isothermally heated quartz bulb volume of 1 l and a rotary speed of 12 revolutions per minute, as described for MI6, in an air stream. The resulting multimetal oxide MI9 was black and had a specific surface area (DIN 66131) of 5.7 m²/g.

Figure 17:
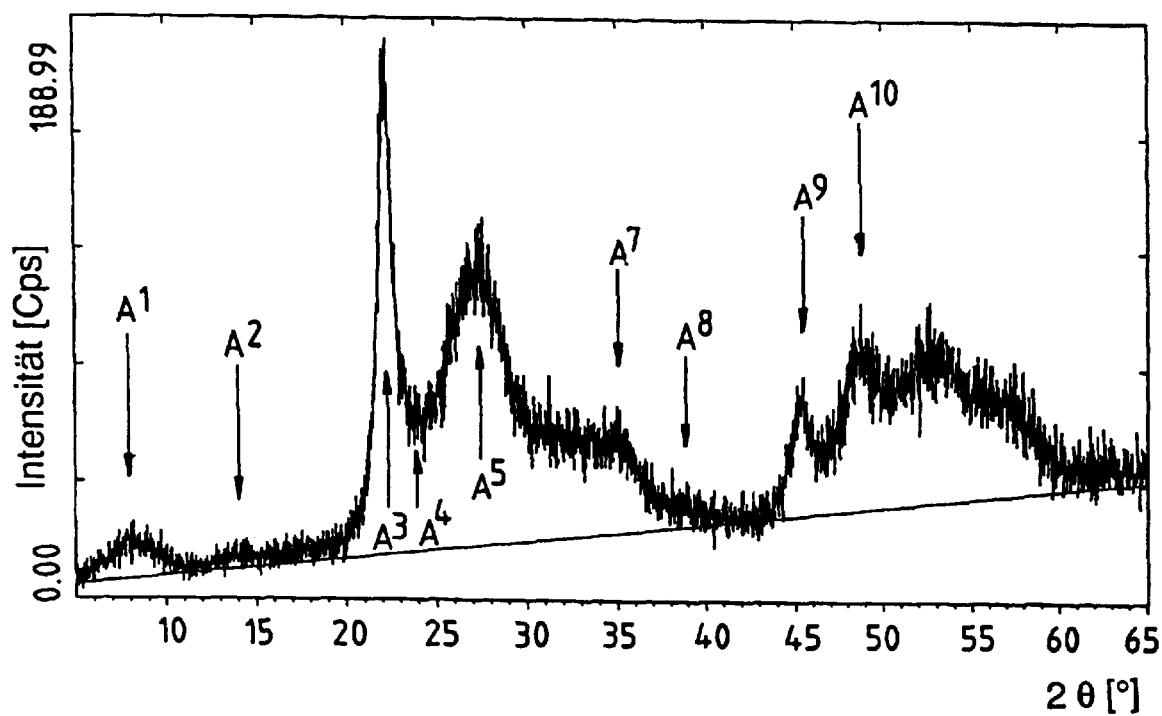
FIG. 17 shows the Cu Kα X-ray powder diffraction pattern of another multimetal oxide of the present invention.

31% of vanadium contained in the multimetal oxide MI9 were present as $V^{4+}$ and 69% as $V^{5+}$. The multimetal oxide MI9 thus had the stoichiometry $Mo_{9.0}V_{3.0}O_{34.04}$. The visual appearance of the associated CuKα X-ray powder diffraction spectrum (FIG. 17) corresponded to that of MI1 and had the three-dimensional atomic arrangement in common with MI1. Its evaluation carried out as for MI1 gave the following diffraction lines in the relevant 2Θ range:

1. Visually resolved:

| X-ray diffraction line | 2Θ [°] | $I_A^{rel}$ [%] |
|---|---|---|
| $A^1$ | 8.0 | 8 |
| $A^2$ | 14.2 | 2 |
| $A^3$ | 22.3 | 100 |
| $A^4$ | 23.9 | 29 |
| $A^5$ | 27.4 | 59 |
| $A^6$ | — | — |
| $A^7$ | 35.0 | 20 |
| $A^8$ | 38.8 | 9 |
| $A^9$ | 45.4 | 23 |
| $A^{10}$ | 48.8 | 32 |

2. Mathematically resolved:

| X-ray diffraction line | 2Θ [°] | $I_F^{rel}$ [%] | FWHM [°] |
|---|---|---|---|
| $A^{1*}$ | 8.1 | 9 | 3.1 |
| $A^{2*}$ | 14.0 | 9 | 2.2 |
| $A^{3*}$ | 22.2 | 43 | 0.9 |
| $A^{4*}$ | 23.3 | 37 | 2.6 |
| $A^{5*}$ | 27.2 | 100 | 3.9 |
| $A^{6*}$ | 31.8 | 25 | 3.9 |
| $A^{7*}$ | 35.1 | 90 | 4.1 |
| $A^{8*}$ | — | — | — |
| $A^{9*}$ | 45.3 | 10 | 1.4 |
| $A^{10*}$ | 48.6 | 24 | 2.5 |

VMI2: $Mo_{9.0}V_{3.0}O_{32.90}$ 100 g of the spray-dried powder from MI8 were calcined in a horizontal rotary kiln with an isothermally heated quartz bulb volume of 1 l and a rotary speed of 12 revolutions per minute, as described for MI1.

Figure 18:
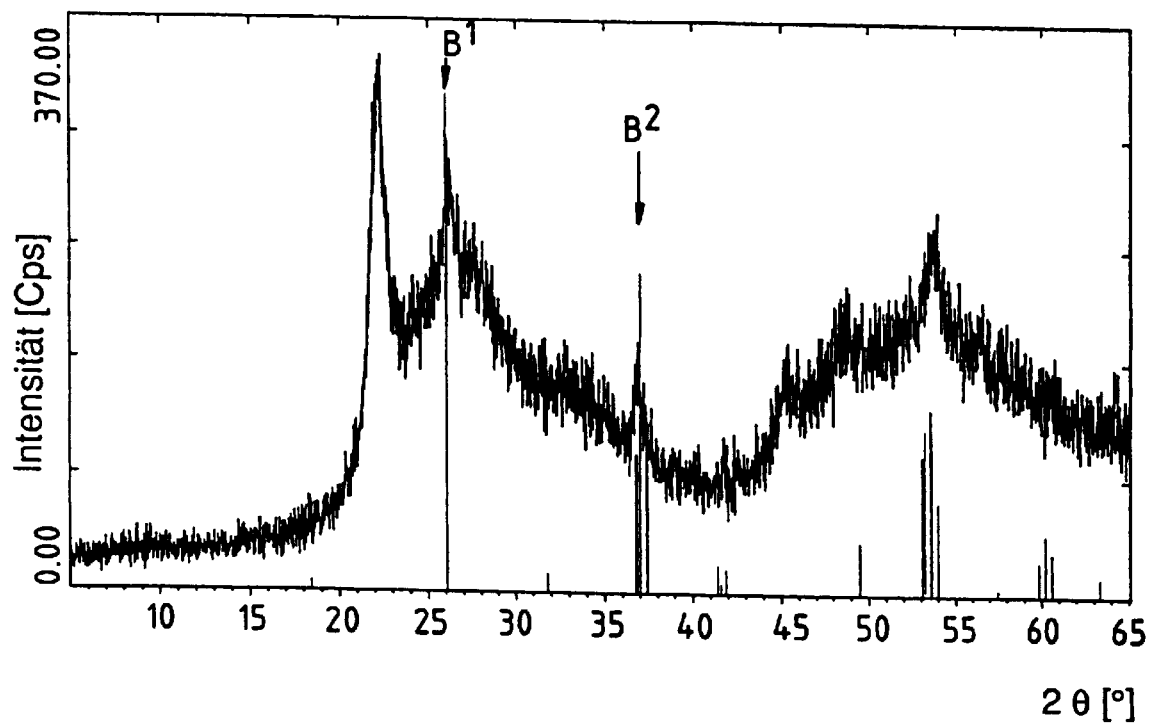
FIG. 18 shows the Cu Kα X-ray powder diffraction pattern of another comparative example.

The resulting multimetal oxide VMI2 was black and had a specific surface area (DIN 66131) of 6.8 m²/g. 93% of the vanadium contained in the multimetal oxide VMI2 were present as $V^{4+}$ and 7% as $V^{3+}$. The visual appearance of the associated CuKα X-ray powder diffraction spectrum evidently differed from that of the multimetal oxide MI1 (cf. FIG. 18) and, in the 2Θ range from 5 to 50°, contained, for example, the following intense diffraction lines:

Visually evaluated:

| X-ray diffraction line | 2Θ [°] | $I_A^{rel}$ [%] | FWHM [°] |
|---|---|---|---|
| B1 | 26.0 | 85 | 0.50 |
| B2 | 36.9 | 31 | 0.45 |

2) Preparation of multimetal oxides II

MII1: Starting Material 1 ($Cu_{12}Mo_{12}O_{48}$) of M5 of DE-A 4 440 891 was Reworked 55.3 g of copper (II) oxide (CuO, from Merck, Darmstadt, ultrapure, at least 96%, pulverulent) and 100.0 g of molybdenum (VI) oxide ($MoO_3$, from Merck, Darmstadt, analytical grade, at least 99.5%, pulverulent) were dispersed in 500 ml of water. The total amount of the aqueous dispersion was heated to 350° C. in an autoclave (material: Hastelloy C4; internal volume: 2.5 l) while stirring (1000 revolutions per minute) and kept at this temperature and at the associated excess pressure for 24 hours while stirring. The autoclave was then cooled to room temperature, the aqueous dispersion contained therein was removed, and the dispersed solid was filtered off and then dried in a drying oven at 80° C. In the investigation by scanning electron microscopy (SEM), the resulting dry powder exhibited crystalline particles having a number average particle diameter of about 8 μm. The chemical analysis of the crystalline particle gave a Cu/Mo ratio of about 1.

With the use of CuKα radiation (Siemens D-5000 diffractometer, 40 kV, 30 mA, with automatic divergence, scatter and counter tube collimator and Peltier detector), the crystalline powder $CuMoO_y$ gave the following X-ray diffraction pattern, reproduced in the form of interplanar spacings d[Å], independent of the wavelength of the X-rays used, and the associated relative intensities (%) of the various diffraction lines, based on the diffraction line with the strongest intensity (amplitude):

| d [Å] | $I_A^{rel}$ [%] |
|---|---|
| 2.44 | 100 |
| 3.01 | 58.4 |
| 3.14 | 56.8 |
| 2.75 | 35.5 |
| 2.82 | 30.6 |
| 3.39 | 30.1 |
| 1.65 | 25.2 |
| 3.96 | 21.6 |
| 1.72 | 21.1 |
| 2.50 | 20.5 |
| 2.20 | 17.3 |
| 4.68 | 15.2 |
| 2.48 | 14.5 |
| 1.96 | 13.8 |
| 3.71 | 13.7 |
| 3.75 | 13.2 |
| 1.80 | 12.4 |
| 2.90 | 12.2 |
| 2.34 | 12.1 |
| 1.61 | 11.8 |
| 1.59 | 11.6 |
| 3.31 | 11.5 |
| 1.85 | 11.5 |
| 2.04 | 11.3 |
| 2.08 | 11.2 |
| 1.70 | 11.1 |
| 2.00 | 10.8 |
| 1.89 | 10.7 |
| 2.12 | 10.3 |
| 1.88 | 9.15 |
| 1.86 | 8.52 |
| 1.98 | 8.25 |
| 2.30 | 8.01 |
| 2.04 | 7.29 |
| 2.66 | 6.89 |
| 1.57 | 6.73 |
| 1.55 | 6.54 |
| 1.77 | 6.53 |
| 2.37 | 6.45 |
| 1.56 | 6.03 |
| 1.55 | 5.93 |
| 3.45 | 5.82 |
| 2.12 | 5.79 |
| 1.63 | 5.76 |
| 2.06 | 5.72 |
| 1.83 | 5.43 |
| 1.60 | 5.42 |
| 2.14 | 5.12 |
| 5.81 | 4.91 |

The uncertainty of the stated interplanar spacings d is ±0.20 Å (the lines of low intensity presumably also include lines due to slight impurities). This X-ray diffraction pattern corresponds to that for $CuMoO_4$-III in Russian Journal of Inorganic Chemistry 36 (7) (1991), 927, Table 1.

MII2: Starting Material 1 ($Cu_{12}Mo_6W_6O_{42-48}$) of M3 of DE-A 19528646 was Reworked 223.05 g of ammonium heptamolybdate hydrate ($MoO_3$ content: 81.3% by weight, ideal composition: $(NH_4)_6Mo_7O_{24} \cdot 4H_2O$) and 327.52 g of ammonium paratungstate hydrate ($WO_3$ content: 89.2% by weight, ideal composition: $(NH_4)_{10}W_{12}O_{41} \cdot 7H_2O$) were dissolved in 5 l of water at 90° C. while stirring (solution A). 3 l of water and 197.88 g of a 25% strength by weight aqueous ammonia solution were added to 492.64 g of copper acetate hydrate (Cu content: 32.5% by weight, ideal composition: $Cu(CH_3COO)_2 \cdot H_2O$) and stirring was carried out for 15 minutes at 25° C., a light blue suspension being obtained (suspension B). The suspension B was then stirred into the solution A which was at 90° C., and the resulting suspension was stirred for a further 3 hours at 80° C. After cooling to 25° C., the aqueous suspending medium of the resulting aqueous suspension (suspension C) had a pH (glass electrode) of 5.3. The suspension C was spray-dried at an inlet temperature of 310° C. and an outlet temperature of 110° C. The green powder obtained was calcined in air, heating being effected continuously from 25 to 300° C. within 24 hours in a first step and continuously from 300 to 780° C. within 3 hours in a subsequent second step, and the temperature being kept at 780° C. for a further hour in a third step. Calcination was carried out in a rotary kiln having an effective volume of 1 l, in each case 60 g of starting spray powder being used and an air flow of 50 l (S.T.P.)/h being established.

The resulting powder had a brown color and a specific surface area according to DIN 66131 of 0.3 $m^2/g$ and the composition $Cu_{12}Mo_6W_6O_{42-48}$. In the investigation by SEM, the powder exhibited crystalline particles having a number average particle diameter of about 8 $\mu m$. With the use of $CuK\alpha$ radiation (Siemens D-5000 diffractometer, 40 kV, 30 mA, with automatic divergence, scatter and counter tube collimator and Peltier detector), the crystalline powder gave an X-ray powder diagram which exhibited a superposition of the wolframite fingerprint on the HT copper molybdate fingerprint, ie. it had a two-phase structure. According to the line intensities, the two structure types were present roughly in the frequency ratio 60 (wolframite structure): 40 (HT copper molybdate type).

The HT copper molybdate structure type is characterized by the following X-ray diffraction diagram, recorded with a crystalline powder of the composition $CuMo_{0.9}W_{0.1}O_{3.5-4}$ with the use of $CuK\alpha$ radiation (Siemens D-5000 diffractomer, 48 kV, 30 mA, with automatic divergence, scatter and counter tube collimator and Peltier detector) and reproduced in the form of interplanar spacings d[Å], independent of the wavelength of the X-rays used, and the associated relative intensities (%), based on the diffraction line of strongest intensity (amplitude), of the various diffraction lines (arranged according to decreasing intensity):

| d [Å] | $I_A^{rel}$ [%] |
|---|---|
| 3.40 | 100 |
| 3.54 | 72 |
| 2.27 | 39 |
| 6.79 | 32 |
| 2.56 | 25 |
| 1.57 | 22 |
| 1.87 | 19 |
| 2.96 | 18 |
| 3.56 | 18 |
| 1.64 | 17 |
| 2.66 | 16 |
| 1.59 | 16 |
| 1.55 | 16 |
| 2.67 | 14 |
| 2.00 | 14 |
| 3.04 | 13 |
| 1.57 | 11 |
| 2.36 | 11 |
| 1.44 | 11 |
| 1.70 | 10 |
| 1.51 | 10 |
| 2.35 | 10 |
| 1.55 | 9.6 |
| 2.32 | 9.2 |
| 2.89 | 9.0 |
| 1.68 | 9.0 |

-continued

| d [Å] | $I_A^{rel}$ [%] |
|---|---|
| 1.48 | 8.9 |
| 1.94 | 8.7 |
| 1.60 | 8.7 |
| 2.69 | 8.6 |
| 1.84 | 8.5 |
| 1.99 | 8.1 |
| 3.92 | 8.0 |
| 2.34 | 8.0 |
| 2.70 | 7.5 |
| 1.52 | 7.5 |
| 1.49 | 7.4 |
| 2.44 | 7.3 |
| 5.78 | 7.2 |
| 1.68 | 7.1 |
| 1.91 | 6.9 |
| 1.71 | 6.8 |
| 1.74 | 6.5 |
| 4.56 | 6.3 |
| 3.16 | 6.1 |
| 2.08 | 5.7 |
| 2.02 | 5.6 |
| 2.28 | 5.6 |
| 2.05 | 5.5 |
| 1.80 | 5.4 |
| 5.13 | 4.9 |
| 3.48 | 4.9 |
| 3.12 | 4.1 |
| 4.20 | 3.7 |
| 4.39 | 3.5 |
| 3.84 | 3.5 |
| 3.73 | 3.4 |
| 4.68 | 3.4 |
| 4.46 | 3.2 |
| 3.76 | 2.9 |

The uncertainty of the stated interplanar spacings d is essentially±0.3 Å for values of ≧2.9 Å and essentially±0.2 Å for d values of <2.9 Å (the low-intensity lines may also include lines due to slight impurities).

3) Preparation of coated catalysts S1 to S3 and comparative coated catalysts SV1 to SV3

S1: After the multimetal oxide MI1 from 1) ($Mo_{8.54}V_{2.47}W_{0.99}O_{33.53}$) had been milled to particle diameters of from 0.1 to 50 μm, nonporous steatite beads having a rough surface, a diameter of from 4 to 5 mm and a peak-to-valley height $R_z$ of from 40 to 200 μm (determined according to DIN 4768, sheet 1, using a Hommel Tester for DIN/ISO surface parameters, from Hommel-werke, Germany) were coated with the resulting active material powder in a rotary drum in an amount of 50 g of powder per 200 g of steatite beads, with simultaneous addition of 18 g of water, according to DE-A 4442346. Drying was then effected with air at 110° C.

SV1: As for S1, except that the multimetal oxide VMI1 from 1) which had been milled in a corresponding manner and likewise had the composition $Mo_{8.54}V_{2.47}W_{0.99}O_{33.53}$ was used as active material.

S2: As for S1, except that a mixture of multimetal oxide MI1 from 1) ($Mo_{12}V_{3.47}W_{1.39}O_{47.11}$), milled in a corresponding manner, and the multimetal oxide powder MII1 from 2) ($Cu_{12}Mo_{12}O_{48}$), milled to a number average maximum particle diameter of from 1 to 3 μm using a centrigual mill from Retsch, Germany, was used as active material. MII1 was stirred into milled MI1 in an amount such that the molar ratio of the abovementioned stoichiometric units in the resulting mixed powder was 6.5 (MI1):1 (MII1). A thorough mixture of the two powders was obtained by mixing in an intensive mixer from Gustav Eirich, Hardheim, Germany (type R02, MPM system). With use of a pan having a volume of 10 l and rotating at 64 revolutions per minute and a Stern impeller which rotated countercurrent to the pan at 900 revolutions per minute, 600 g of mixture were mixed for 15 minutes.

The resulting two-phase active material was:
$[Mo_{12}V_{3.47}W_{1.39}O_{47.11}]_{6.5}[Cu_{12}Mo_{12}O_{48}]\hat{=}$
$Mo_{12}V_3W_{1.2}Cu_{1.6}O_{47.23}$ S3: As for S2, except that the multimetal oxide MII2 from 2) was used instead of the multimetal oxide MII1 from 2).

The resulting active material was:
$[Mo_{12}V_{3.47}W_{1.39}O_{47.11}]_{6.5}[Cu_{12}Mo_6W_6O_{42-48}]$.

SV2: As for S1, except that a finely divided powder produced as follows was used as active material:

127 g of copper (II) acetate monohydrate (32.4% by weight of Cu) were dissolved in 2700 g of water to give a solution I. 860 g of ammonium heptamolybdate tetrahydrate (81.3% by weight of $MoO_3$), 143 g of ammonium metavanadate (77.2% by weight of $V_2O_5$) and 126 g of ammonium paratungstate heptahydrate (89.3% by weight of $WO_3$) were dissolved in succession in 5500 g of water at 95° C. to give a solution II. The solution I was then stirred all at once into the solution II, and the aqueous mixture heated at 80° C. was spray-dried at an outlet temperature of 110° C.

800 g of the spray powder were kneaded and calcined as the 800 g of spray powder for the preparation of MI1. Thereafter, milling was effected to give a particle diameter of from 0.1 to 50 μm, and a coated catalyst was formed as in S1.

Stoichiometry of the active material: $Mo_{12}V_3W_{1.2}Cu_{1.6}O_x$*.

Figure 19:
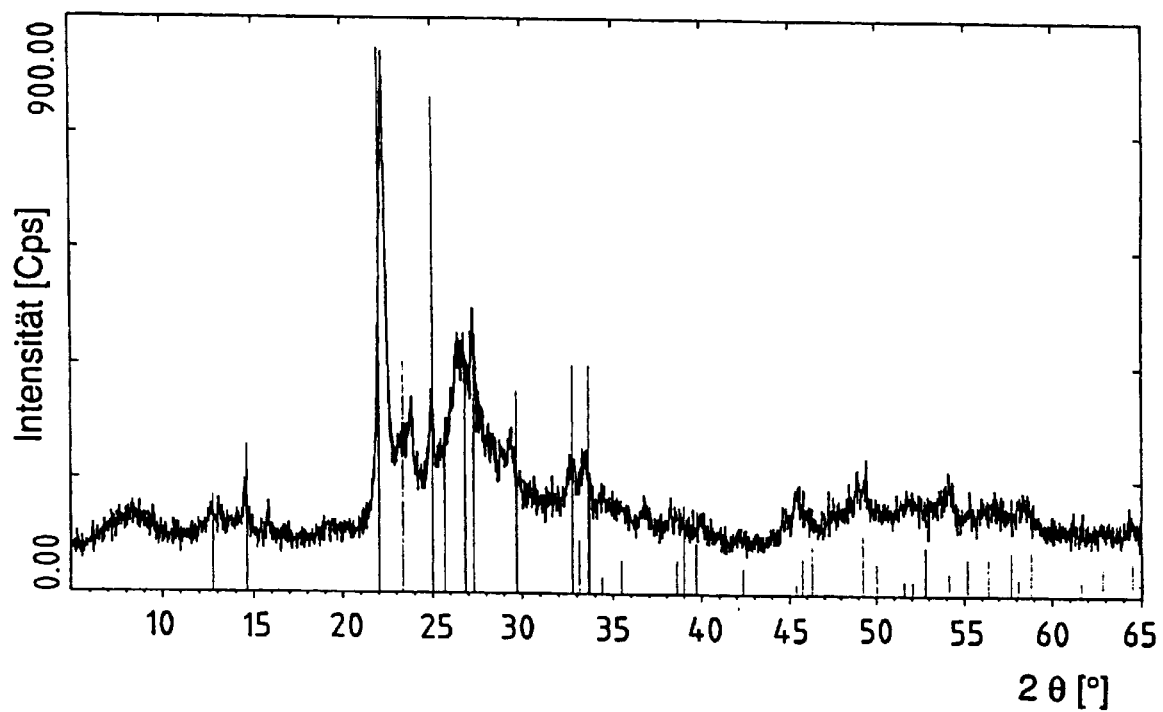
FIG. 19 shows the Cu Kα X-ray powder diffraction pattern of another multimetal oxide of the present invention.

FIG. 19 shows the associated CuKα X-ray powder diffraction spectrum, which differs significantly from that of the multimetal oxide MI1 in that it has X-ray diffraction lines differing from $A^1$ to $A^{10}$ in the range 2⊖5 to 50°.

SV3: As for SV2, except that exclusively 3.6 l (S.T.P.)/h of air flowed through the calcination furnace during the entire calcination time.

Stoichiometry of the active material: $Mo_{12}V_3W_{1.2}Cu_{1.6}O_x$**.

4. Use of the coated catalysts from 3) as catalysts for the gas-phase oxidation of acrolein to acrylic acid.

The catalysts were introduced into a tube reactor (V2A stainless steel, 25 mm internal diameter, 2000 g catalyst bed, heated by means of a salt bath), and a gaseous mixture composed of 5% by volume of acrolein, 7% by volume of oxygen, 10% by volume of steam and 78% by volume of nitrogen was fed in at reaction temperatures of from 250 to 270° C. using a residence time of 2.0 seconds. In all cases, the salt bath temperature was adjusted so that, after forming was complete, a single pass gave a uniform acrolein conversion of 99%. The product gas mixture falling out of the reactor was analyzed by gas chromatography. The results for the selectivity of the acrylic acid formation using different catalysts are shown in the Table below.

| Catalyst | S % | Bath temperature (° C.) |
|---|---|---|
| S1 | 92.4 | 255 |
| SV1 | 92.2 | 264 |
| S2 | 96.0 | 254 |

-continued

| Catalyst | S % | Bath temperature (° C.) |
|---|---|---|
| S3 | 96.5 | 255 |
| SV3 | 95.1 | 261 |
| SV2 | 95.3 | 254 |

The conversion, selectivity and residence time are defined as follows:

$$\text{Conversion C of acrolein (\%)} = \frac{\text{number of moles of converted acrolein}}{\text{number of moles of acrolein used}} \times 100$$

$$\text{Selectivity S of the acrylic acid formation \%} = \frac{\text{converted to acrylic acid}}{\text{total number of moles of acrolein converted}} \times 100;$$

$$\text{Residence time (sec)} = \frac{\text{empty reactor volume filled with catalyst (1)}}{\text{amount of synthesis gas passed through (1(S.T.P.)/h}} \times 3600$$

We claim:

1. A method for gas-phase oxidation of an organic compound, comprising:
   oxidizing said organic compound with an oxidizing agent in the presence of a catalyst, to produce a product;
   wherein said catalyst, comprises:
   a multimetal oxide material having at least two phases and of the formula III $$\{A\}_p\{B\}_q \quad \text{(III)},$$

wherein
   $A=(Mo_{12-a-b-c}V_aM_b^1M_c^2O_x)\times 12$ (active phase), 12-a-b-c
   $B=M_{12}^3Cu_dH_eO_y$ (promoter phase),
   $M^1$ is W or Nb,
   $M^2$ is Ti, Zr, Hf, Ta, Cr, Si or Ge,
   a is from 0.1 to 6,
   b is from 0 to 6,
   c is from 0 to 6,
   with the proviso that a+b+c is from 0.1 to 6,
   x is a number which is determined by the valency and frequency of the elements in A other than oxygen,
   $M^3$ is Mo, W, V, Nb or Ta,
   d is from 4 to 30,
   e is from 0 to 20,
   y is a number which is determined by the valency and frequency of the elements in B other than oxygen,
   p and q are numbers other than zero, whose ratio p/q is from 160:1 to 1:1, which contains the moiety $\{A\}_p$ in the form of three-dimensional regions A which are delimited from their local environment owing to their chemical composition differing from their local environment and are of the chemical composition $$A\ Mo_{12-a-b-c}\ V_a\ M_b^1\ M_c^2\ O_x$$

and the moiety $\{B\}_q$ in the form of three dimensional regions B which are delimited from their local environment owing to their chemical composition differing from their local environment and are of the chemical composition $$B\ M_{12}^3\ Cu_d\ H_e\ O_y$$

where the regions A and B are distributed relative to one another as in a mixture of finely divided A and finely divided B and, with the use of CuKα radiation (λ=1.54178 Å), the three-dimensional atomic arrangement of the regions A gives an X-ray powder diffraction spectrum (the intensity of the diffracted X-rays plotted as a function of twice the diffraction angle (2Θ)) which, in the 2Θ range from 5 to 50°, contains at least the following characteristic diffraction lines $A^1, A^3, A^5, A^9$ and $A^{10}$ but not more than the following diffraction lines $A^1$ to $A^{10}$:

| Diffraction line | 2Θ (°) |
|---|---|
| $A^1$ | 8.3 ± 0.7 |
| $A^2$ | 14.4 ± 0.7 |
| $A^3$ | 22.3 ± 0.2 |
| $A^4$ | 23.5 ± 0.7 |
| $A^5$ | 27.2 ± 0.4 |
| $A^6$ | 32.0 ± 0.8 |
| $A^7$ | 34.8 ± 0.6 |
| $A^8$ | 38.7 ± 0.5 |
| $A^9$ | 45.4 ± 0.4 |
| $A^{10}$ | 48.8 ± 0.4 |

2. The method of claim 1, wherein said organic compound is acrolein, and said product is acrylic acid.

3. A method for gas-phase oxidation of an organic compound, comprising:
   oxidizing said organic compound with an oxidizing agent in the presence of a catalyst, to produce a product;
   wherein said catalyst, comprises:
   a mixture comprising a first multimetal oxide I and a second multimetal oxide, wherein said first multimetal oxide is a multimetal oxide of the formula I $$Mo_{12-a-b-c}\ V_aM_b^1M_c^2O_x \quad \text{(I)},$$

where
   $M^1$ is W and/or Nb,
   $M^2$ is Ti, Zr, Hf, Ta, Cr, Si and/or Ge,
   a is from 0.1 to 6,
   b is from 0 to 6,
   c is from 0 to 6,
   with the proviso that a+b+c is from 0.1 to 6, and
   x is a number which is determined by the valency and frequency of the elements in I other than oxygen,
   whose three-dimensional atomic arrangement obtained using CuKα radiation (λ=1.54178 Å) gives an X-ray powder diffraction spectrum (the intensity A of the diffracted X-rays plotted as a function of twice the diffraction angle (2Θ)) which contains, in the 2Θ range from 5 to 50°, contains at least the following characteristic diffraction lines $A^1, A^3, A^5, A^9$ and $A^{10}$, but at most the following diffraction lines $A^1$ to $A^{10}$:

| X-ray diffraction line | 2Θ (°) |
|---|---|
| $A^1$ | 8.3 ± 0.7 |
| $A^2$ | 14.4 ± 0.7 |

-continued

| X-ray diffraction line | 2Θ (°) |
|---|---|
| $A^3$ | 22.3 ± 0.2 |
| $A^4$ | 23.5 ± 0.7 |
| $A^5$ | 27.2 ± 0.4 |
| $A^6$ | 32.0 ± 0.8 |
| $A^7$ | 34.8 ± 0.6 |
| $A^8$ | 38.7 ± 0.5 |
| $A^9$ | 45.4 ± 0.4 |
| $A^{10}$ | 48.8 ± 0.4 | and said second multimetal oxide is a multimetal oxide of the formula II $$M_{12}^3 Cu_d H_e O_y \qquad (II),$$

where $M^3$ is Mo, W, V, Nb or Ta, d is from 4 to 30, e is from 0 to 20 and y is a number which is determined by the valency and frequency of the elements in II other than oxygen.

4. The method of claim 3, wherein said organic compound is acrolein, and said product is acrylic acid.

5. A method for gas-phase oxidation of an organic compound, comprising:

oxidizing said organic compound with an oxidizing agent in the presence of a catalyst, to produce a product;

wherein said catalyst, comprises:

a multimetal oxide material having at least two phases and of the formula III $$\{A\}_p \{B\}_q \qquad (III),$$

wherein $A = (Mo_{12-a-b-c} V_a M_b^1 M_c^2 O_x) \cdot (12/(12\text{-}a\text{-}b\text{-}c))$ (active phase), $B = M_{12}^3 Cu_d H_e O_y$ (promoter phase), $M^1$ is W or Nb, $M^2$ is Ti, Zr, Hf, Ta, Cr, Si or Ge, a is from 0.1 to 6, b is from 0 to 6, c is from 0 to 6, with the proviso that a+b+c is from 0.1 to 6, x is a number which is determined by the valency and frequency of the elements in A other than oxygen, $M^3$ is Mo, W, V, Nb or Ta, d is from 4 to 30, e is from 0 to 20, y is a number which is determined by the valency and frequency of the elements in B other than oxygen, p and q are numbers other than zero, whose ratio p/q is from 160:1 to 1:1, which contains the moiety $\{A\}_p$ in the form of three-dimensional regions A which are delimited from their local environment owing to their chemical composition differing from their local environment and are of the chemical composition $$A\ Mo_{12-a-b-c}\ V_a M_b^1 M_c^2 O_x$$

and the moiety $\{B\}_q$ in the form of three dimensional regions B which are delimited from their local environment owing to their chemical composition differing from their local environment and are of the chemical composition $$B\ M_{12}^3\ Cu_d\ H_e\ O_y$$

where the regions A and B are distributed relative to one another as in a mixture of finely divided A and finely divided B and a three-dimensional atomic arrangement of the regions A is that of the multimetal oxide $Mo_{8.54}V_{2.47}W_{0.99}O_{33.35}$ which is obtainable as follows:

33.746 kg of ammonium heptamolybdate hydrate ($MoO_3$ content: 81.8% by weight, ideal composition: $(NH_4)_6Mo_7O_{24} \cdot 4\ H_2O$), 6.576 kg of ammonium metavanadate ($V_2O_5$ content: 76.5% by weight, ideal composition: $NH_4VO_3$), 5.764 kg of ammonium paratungstate hydrate ($WO_3$ content: 89.0% by weight, ideal composition: $(NH_4)_{10}W_{12}O_{41} \cdot 7\ H_2O$) and 7.033 kg of ammonium acetate ($CH_3COONH_4$ content: 97.0% by weight, ideal composition: $CH_3CONH_4$) are dissolved in succession in the stated order in 250 l of water at 90° C. while stirring; the resulting yellow to orange solution is cooled to 80° C. and spray-dried at an inlet temperature of 300° C. and an outlet temperature of 110° C;

800 g of the spray powder obtained are kneaded in a kneader (type LUK 2.5 from Werner and Pfleiderer, 7000 Stuttgart, Germany) having an effective volume of 2.5 l, with the addition of 250 g of water, for 1 hour. Of the 250 g of water, 180 g are added within the first 10 minutes of kneading and 70 g within the remaining 50 minutes of kneading; the resulting moist and clod-like kneaded product is dried for 15 hours at 110° C. and then forced through a sieve having a mesh size of 5 mm:

100 g of the resulting granules are then calcined in a horizontal rotary kiln with an isothermally heated quartz bulb volume of 1 l and a rotary speed of 12 revolutions per minute, the calcination conditions being as follows:

$1^{st}$ step: the granules used are continuously heated from 25 to 275° C. within 50 minutes;

$2^{nd}$ step: the granules used are continuously heated from 275 to 325° C. within 30 minutes;

$3^{rd}$ step: the granules used are kept at 325° C. for 4 hours;

$4^{th}$ step: the granules used are continuously heated from 325 to 400° C. within 30 minutes;

$5^{th}$ step: the granules used are kept at 400° C. for 10 minutes;

the external heating of the rotary kiln is then switched off and the latter is cooled by blowing on surrounding air from the outside; the granules used cool to 25° C. in the course of 5 hours;

during the individual calcination steps, gas mixtures which have the following compositions (standard temperature and pressure conditions (S.T.P.) 1 atm, 25° C.) flow through the interior of the rotary kiln, parallel to the axis of rotation:

$1^{st}$ step, $2^{nd}$ step and $3^{rd}$ step:

3.6 l (S.T.P.)/h or air, 1.5 l (S.T.P.)/h of $NH_3$ and 44.9 l (S.T.P.)/h of $N_2$ (total gas flow: 50 l (S.T.P.)/h):

$4^{th}$ step, $5^{th}$ step and cooling phase:

3.6 l (S.T.P.)/h of air and 44.9 l (S.T.P.)/h of $N_2$ (total gas flow: 48.5 l (S.T.P.)/h).

6. The method of claim 5, wherein said organic compound is acrolein, and said product is acrylic acid.

7. A method for gas-phase oxidation of an organic compound, comprising:

oxidizing said organic compound with an oxidizing agent in the presence of a catalyst, to produce a product;

wherein said catalyst, comprises:
a multiphase composition, comprising homogeneously distributed regions having a maximum diameter of from >0 to 300 µm of a multimetal oxide of the formula I $$Mo_{12-a-b-c}V_aM^1_bM^2_cO_x \qquad (I),$$

where $M^1$ is W or Nb, $M^2$ is Ti, Zr, Hf, Ta, Cr, Si and/or Ge, a is from 0.1 to 6, b is from 0 to 6, c is from 0 to 6, with the proviso that a+b+c is from 0.1 to 6, and x is a number which is determined by the valency and frequency of the elements in I other than oxygen, whose three-dimensional atomic arrangement obtained using CuKα radiation (λ=1.54178 Å) gives an X-ray powder diffraction spectrum (the intensity A of the diffracted X-rays plotted as a function of twice the diffraction angle (2Θ)) which contains, in the 2Θ range from 5 to 50°, contains at least the following characteristic diffraction lines $A^1$, $A^3$, $A^5$, $A^9$ and $A^{10}$, but at most the following diffraction lines $A^1$ to $A^{10}$:

| X-ray diffraction line | 2Θ (°) |
|---|---|
| $A^1$ | 8.3 ± 0.7 |
| $A^2$ | 14.4 ± 0.7 |
| $A^3$ | 22.3 ± 0.2 |
| $A^4$ | 23.5 ± 0.7 |
| $A^5$ | 27.2 ± 0.4 |
| $A^6$ | 32.0 ± 0.8 |
| $A^7$ | 34.8 ± 0.6 |
| $A^8$ | 38.7 ± 0.5 |
| $A^9$ | 45.4 ± 0.4 |
| $A^{10}$ | 48.8 ± 0.4 |

8. The method of claim 7, wherein said organic compound is acrolein, and said product is acrylic acid.

9. A method for gas-phase oxidation of an organic compound, comprising:
oxidizing said organic compound with an oxidizing agent in the presence of a catalyst, to produce a product;
wherein said catalyst, comprises a multimetal oxide material, comprising:
at least two phases and of the formula III $$\{A\}_p\{B\}_q \qquad (III),$$

wherein $A=(Mo_{12-a-b-c}V_aM^1_bM^2_cO_x)\times 12$ (active phase), 12-a-b-c $B=M^3_{12}Cu_dH_eO_y$ (promoter phase), $M^1$ is W or Nb, $M^2$ is Ti, Zr, Hf, Ta, Cr, Si or Ge, a is from 0.1 to 6, b is from 0 to 6, c is from 0 to 6, with the proviso that a+b+c is from 0.1 to 6, x is a number which is determined by the valency and frequency of the elements in A other than oxygen, $M^3$ is Mo, W, V, Nb or Ta, d is from 4 to 30, e is from 0 to 20, y is a number which is determined by the valency and frequency of the elements in B other than oxygen, p and q are numbers other than zero, whose ratio p/q is from 160:1 to 1:1, which contains the moiety $\{A\}_p$ in the form of three-dimensional regions A which are delimited from their local environment owing to their chemical composition differing from their local environment and are of the chemical composition $$A \; Mo_{12-a-b-c} \; V_a \; M^1_b \; M^2_c \; O_x$$

and the moiety $\{B\}_q$ in the form of three dimensional regions B which are delimited from their local environment owing to their chemical composition differing from their local environment and are of the chemical composition $$B \; M^3_{12} \; Cu_d \; H_e \; O_y$$

where the regions A and B are distributed relative to one another as in a mixture of finely divided A and finely divided B and, with the use of CuKα radiation (λ=1.54178 Å), the three-dimensional atomic arrangement of the regions A gives an X-ray powder diffraction spectrum (the intensity of the diffracted X-rays plotted as a function of twice the diffraction angle (2Θ)) which, in the 2Θ range from 5 to 50°, contains at least the following characteristic diffraction lines $A^1$, $A^3$, $A^5$, $A^9$ and $A^{10}$ but not more than the following diffraction lines $A^1$ to $A^{10}$:

| Diffraction line | 2Θ (°) |
|---|---|
| $A^1$ | 8.3 ± 0.7 |
| $A^2$ | 14.4 ± 0.7 |
| $A^3$ | 22.3 ± 0.2 |
| $A^4$ | 23.5 ± 0.7 |
| $A^5$ | 27.2 ± 0.4 |
| $A^6$ | 32.0 ± 0.8 |
| $A^7$ | 34.8 ± 0.6 |
| $A^8$ | 38.7 ± 0.5 |
| $A^9$ | 45.4 ± 0.4 |
| $A^{10}$ | 48.8 ± 0.4 | whose region B has the structure type of at least one of the copper molybdates selected from the group consisting of (the expression in brackets indicates the source of the associated X-ray diffraction fingerpring):

$Cu_3(MoO_4)_2(OH)_2$ (Lindgrenite, index card 36-405 of the JCPDS-ICDD index (1991)), $Cu_4MoO_6O_{20}$ (A. Moini et al., Inorg. Chem 25 (21) (1986) pages 3782 to 3785), $Cu_4Mo_5O_{17}$ (Index card 39-181 of the JCPDS-ICDD index (1991)), $Cu_6Mo_5O_{18}$ (Index card 40-865 of the JCPDS-ICDD index (1991)), $Cu_6Mo_4O_{15}$ (Index card 35-17 of the JCPDS-ICDD index (1991)), $CuMoO_4$ (Index card 22-242 of the JCPDS-ICDD index (1991)), $CuMoO_4$ (Russian Journal of Inorganic Chemistry 36(7) (1991), 927–928, Table 1, $CuMoO_4$-III with distorted wolfrramite structure ($CuWO_4$, index card 21-307 of the JCPDS-ICDD index (1994)), $CuMoO_4$ (Index card 26-546 of the JCPDS-ICDD index (1991)), HT-Cu molybdate (DE-A 19 528 646), $Cu_{4-x}Mo_3O_{12}$ where x is from 0 to 0.25 (index cards 24-56 and 26-547 of the JCPDS-ICDD index (1991)), $Cu_3Mo_2O_9$ (Index cards 24-55 and 34-637 of the JCPDS-ICDD index (1991)), and $Cu_2MoO_5$ (Index cards 22-607 of the JCPDS-ICDD index (1991)).

10. The method of claim 9, wherein said organic compound is acrolein, and said product is acrylic acid.

* * * * *